(12) United States Patent
Papp et al.

(10) Patent No.: US 9,895,244 B2
(45) Date of Patent: Feb. 20, 2018

(54) SEGMENTED SCAFFOLDS AND DELIVERY THEREOF FOR PERIPHERAL APPLICATIONS

(71) Applicant: Abbott Cardiovascular Systems Inc., Santa Clara, CA (US)

(72) Inventors: John E. Papp, Temecula, CA (US); Hung T. Nguyen, San Diego, CA (US); Justin K. Elerath, Temecula, CA (US); Dion I. Herabadi, Temecula, CA (US); Michael T. Martins, Murrieta, CA (US); Kirsten S. King, Lake Oswego, OR (US); Scott H. Mueller, Escondido, CA (US); Coeta K. Peloquin, Fallbrook, CA (US); Stephen D. Pacetti, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/979,297

(22) Filed: Dec. 22, 2015

(65) Prior Publication Data
US 2016/0184120 A1    Jun. 30, 2016

Related U.S. Application Data

(62) Division of application No. 13/441,756, filed on Apr. 6, 2012, now Pat. No. 9,254,212.

(51) Int. Cl.
*A61F 2/06* (2013.01)
*A61F 2/958* (2013.01)
(Continued)

(52) U.S. Cl.
CPC .............. *A61F 2/958* (2013.01); *A61F 2/844* (2013.01); *A61F 2/91* (2013.01); *A61F 2/915* (2013.01);
(Continued)

(58) Field of Classification Search
CPC .... A61F 2/958; A61F 2002/9522; A61F 2/00; A61F 2002/826; A61F 2/966;
(Continued)

(56) References Cited

U.S. PATENT DOCUMENTS 5,195,984 A * 3/1993 Schatz ...................... A61F 2/91
                                                       604/103.05
5,486,546 A    1/1996 Mathiesen et al.
(Continued)

FOREIGN PATENT DOCUMENTS

EP    0 714 640    6/1996
EP    0 747 088    12/1996
(Continued)

OTHER PUBLICATIONS

International Search Report for PCT/US2011/047574, dated Nov. 7, 2011, 3 pgs.
(Continued)

*Primary Examiner* — Amy R Weisberg
(74) *Attorney, Agent, or Firm* — Squire Patton Boggs (US) LLP

(57) ABSTRACT

Segmented scaffolds composed of disconnected scaffold segments are delivered to an implant site on a delivery balloon. The segments are crimped to the balloon and separated from each other by gaps. When the balloon is inflated the gaps between the disconnected scaffold segments stay constant. Pillowed or banded balloons are used to deliver the segments.

13 Claims, 25 Drawing Sheets

(51) Int. Cl.
*A61F 2/966* (2013.01)
*A61F 2/844* (2013.01)
*A61F 2/91* (2013.01)
*A61F 2/915* (2013.01)
*A61F 2/82* (2013.01)

(52) U.S. Cl.
CPC ........ *A61F 2/966* (2013.01); *A61F 2002/826* (2013.01); *A61F 2002/9583* (2013.01); *A61F 2210/0076* (2013.01); *A61F 2250/0019* (2013.01); *A61F 2250/0039* (2013.01)

(58) Field of Classification Search
CPC ...... A61F 2250/0039; A61F 2210/0076; A61F 2250/0019; A61F 2002/9583; Y10T 29/49913; Y10T 29/49908; Y10T 29/49934; Y10T 29/49865; Y10T 29/49925; Y10T 29/49911; B23P 11/005; A61M 25/1002; A61M 25/1011
USPC ............... 606/108, 194; 604/103.06, 103.08, 604/103.05, 96.01; 623/1.11–1.12; 29/515, 520, 505, 508
See application file for complete search history.

(56) References Cited

U.S. PATENT DOCUMENTS

| | | | |
|---|---|---|---|
| 5,669,932 A * | 9/1997 | Fischell | A61F 2/91 606/198 |
| 5,707,385 A | 1/1998 | Williams | |
| 5,836,965 A * | 11/1998 | Jendersee | A61F 2/958 604/103.07 |
| 5,843,117 A * | 12/1998 | Alt | A61F 2/86 606/194 |
| 5,919,893 A | 7/1999 | Roby et al. | |
| 5,935,135 A * | 8/1999 | Bramfitt | A61F 2/958 606/191 |
| 5,972,027 A | 10/1999 | Johnson | |
| 6,174,329 B1 | 1/2001 | Callol et al. | |
| 6,187,034 B1 * | 2/2001 | Frantzen | A61F 2/91 623/1.11 |
| 6,258,117 B1 * | 7/2001 | Camrud | A61F 2/82 623/1.16 |
| 6,773,447 B2 * | 8/2004 | Laguna | A61M 25/1002 606/198 |
| 7,004,963 B2 * | 2/2006 | Wang | A61F 2/958 606/192 |
| 7,137,993 B2 * | 11/2006 | Acosta | A61F 2/915 623/1.11 |
| 7,169,178 B1 | 1/2007 | Santos et al. | |
| 7,175,873 B1 | 2/2007 | Roorda et al. | |
| 7,192,440 B2 * | 3/2007 | Andreas | A61F 2/958 623/1.11 |
| 7,294,146 B2 | 11/2007 | Chew et al. | |
| 7,357,942 B2 | 4/2008 | Burke et al. | |
| 7,481,835 B1 | 1/2009 | Pacetti et al. | |
| 7,625,401 B2 | 12/2009 | Clifford et al. | |
| 7,892,273 B2 * | 2/2011 | George | A61F 2/915 623/1.11 |
| 7,964,210 B2 | 6/2011 | Wang et al. | |
| 8,046,897 B2 * | 11/2011 | Wang | A61F 2/958 29/505 |
| 8,486,132 B2 * | 7/2013 | Snow | A61F 2/91 623/1.11 |
| 2001/0044651 A1 | 11/2001 | Steinke et al. | |
| 2002/0055768 A1 | 5/2002 | Hess et al. | |
| 2002/0065553 A1 | 5/2002 | Weber et al. | |
| 2002/0111590 A1 | 8/2002 | Davila et al. | |
| 2003/0040771 A1 | 2/2003 | Hyodoh et al. | |
| 2003/0040772 A1 | 2/2003 | Hyodoh et al. | |
| 2003/0055378 A1 | 3/2003 | Wang et al. | |
| 2003/0074049 A1 | 4/2003 | Hoganson et al. | |
| 2003/0083740 A1 | 5/2003 | Pathak | |
| 2003/0181973 A1 | 9/2003 | Sahota | |
| 2003/0199969 A1 | 10/2003 | Steinke et al. | |
| 2004/0034409 A1 | 2/2004 | Heublein et al. | |
| 2004/0093077 A1 | 5/2004 | White et al. | |
| 2004/0147998 A1 | 7/2004 | Nolting | |
| 2004/0167616 A1 | 8/2004 | Camrud et al. | |
| 2004/0186551 A1 | 9/2004 | Kao et al. | |
| 2004/0215331 A1 | 10/2004 | Chew et al. | |
| 2004/0249435 A1 | 12/2004 | Andreas et al. | |
| 2005/0033399 A1 | 2/2005 | Richter | |
| 2005/0080474 A1 | 4/2005 | Andreas et al. | |
| 2005/0096722 A1 * | 5/2005 | Lootz | A61F 2/91 623/1.11 |
| 2005/0125051 A1 | 6/2005 | Eidenschink et al. | |
| 2005/0182479 A1 | 8/2005 | Bonsignore et al. | |
| 2006/0034888 A1 | 2/2006 | Pacetti et al. | |
| 2006/0122691 A1 | 6/2006 | Richter | |
| 2006/0206190 A1 * | 9/2006 | Chermoni | A61F 2/958 623/1.11 |
| 2006/0217795 A1 | 9/2006 | Besselink et al. | |
| 2006/0229700 A1 * | 10/2006 | Acosta | A61F 2/915 623/1.11 |
| 2007/0067012 A1 | 3/2007 | George et al. | |
| 2007/0182041 A1 | 8/2007 | Rizk et al. | |
| 2007/0219612 A1 * | 9/2007 | Andreas | A61B 17/12022 623/1.11 |
| 2007/0219613 A1 | 9/2007 | Kao et al. | |
| 2007/0219642 A1 | 9/2007 | Richter | |
| 2007/0254012 A1 | 11/2007 | Ludwig et al. | |
| 2007/0276464 A1 | 11/2007 | Valencia et al. | |
| 2007/0283552 A1 | 12/2007 | Gale et al. | |
| 2007/0299510 A1 | 12/2007 | Venkatraman et al. | |
| 2008/0015686 A1 | 1/2008 | Gale et al. | |
| 2008/0077229 A1 * | 3/2008 | Andreas | A61F 2/95 623/1.11 |
| 2008/0147165 A1 | 6/2008 | Hossainy et al. | |
| 2008/0243228 A1 | 10/2008 | Wang et al. | |
| 2008/0269865 A1 * | 10/2008 | Snow | A61F 2/958 623/1.11 |
| 2008/0275537 A1 | 11/2008 | Limon | |
| 2009/0012604 A1 | 1/2009 | Schmitz et al. | |
| 2009/0069878 A1 | 3/2009 | Weber et al. | |
| 2009/0088835 A1 | 4/2009 | Wang | |
| 2009/0182415 A1 | 7/2009 | Wang | |
| 2009/0248131 A1 | 10/2009 | Greenan | |
| 2009/0286761 A1 * | 11/2009 | Cheng | A61F 2/91 514/171 |
| 2010/0004735 A1 | 1/2010 | Yang et al. | |
| 2010/0010622 A1 | 1/2010 | Lowe et al. | |
| 2010/0026223 A1 | 2/2010 | Liu et al. | |
| 2010/0191323 A1 | 7/2010 | Cox | |
| 2010/0256728 A1 | 10/2010 | Peterson | |
| 2010/0324667 A1 | 12/2010 | King | |
| 2011/0060401 A1 | 3/2011 | Hoerstrup et al. | |
| 2011/0066222 A1 | 3/2011 | Wang et al. | |
| 2011/0190871 A1 | 8/2011 | Trollsas | |
| 2011/0190872 A1 | 8/2011 | Anukhin et al. | |
| 2012/0035705 A1 * | 2/2012 | Giasolli | A61F 2/86 623/1.12 |
| 2012/0042501 A1 | 2/2012 | Wang et al. | |
| 2013/0268045 A1 * | 10/2013 | Papp | A61F 2/958 623/1.11 |
| 2014/0046431 A1 * | 2/2014 | Papp | A61F 2/89 623/1.16 |
| 2014/0364935 A1 * | 12/2014 | Eli | A61F 2/91 623/1.12 |

FOREIGN PATENT DOCUMENTS

| | | |
|---|---|---|
| EP | 1 000 592 | 5/2000 |
| EP | 1 958 598 | 8/2008 |
| WO | WO 96/33677 | 10/1996 |
| WO | WO 2007/092417 | 8/2007 |
| WO | WO 2008/028964 | 3/2008 |

(56) References Cited

FOREIGN PATENT DOCUMENTS

| WO | WO 2009/137786 | 11/2009 |
| WO | WO 2009/147653 | 12/2009 |
| WO | WO 2013/025470 | 2/2013 |

OTHER PUBLICATIONS

Kuraishi et al., "Development of nanofiber-covered stents using electrospinning: in vitro and acute phase in vivo experiments", J. of biomedical materials res. Part B. Applied biomaterials (2009) Abstract 1 pg.
Loo et al., "Radiation effects on poly(lactide-co-glycolide) and poly-l-lactide", Polymer degradation and stability vol. 83, pp. 259-265 (2005).
Van Vlack, Elements of Materials Science and Engineering 6$^{th}$ Ed., Addison-Wesley Publishing Co, pp. 270-271 (1989).
Wang et al., "Polyethylene-Poly(L-lactide) Diblock Copolymers: Synthesis and Compatibilization of Poly(L-lactide)/Polyethylene Blends", J. of Polymer Science vol. 39, issue 16, pp. 2755-2766 (2001).
Yoshioka et al., "Drug release from pol(d-l-lactide) microspheres by gamma irradiation", J. of controller release vol. 37, pp. 263-267 (1995).
International Search Report and Written Opinion for PCT/US2012/053969, dated Feb. 12, 2014, 24 pgs.

\* cited by examiner

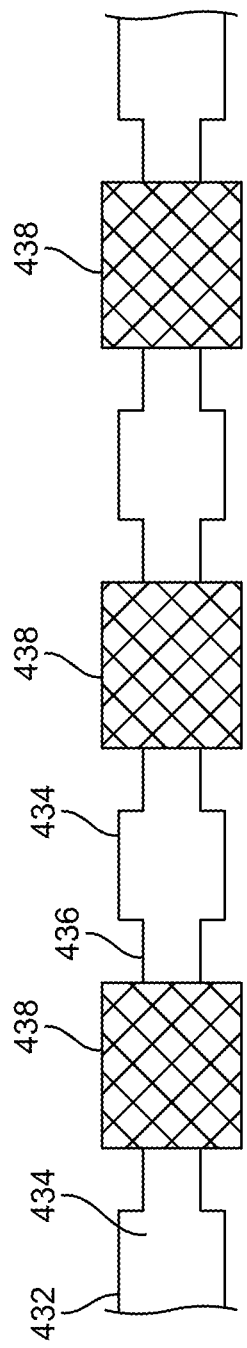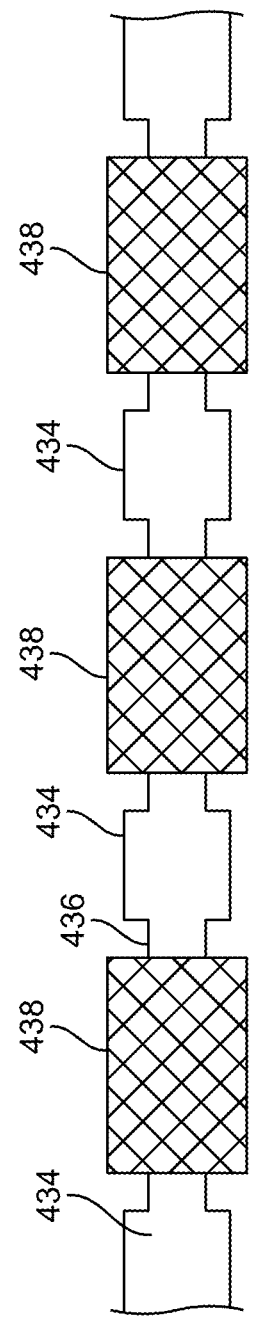
FIG. 10A
FIG. 10B

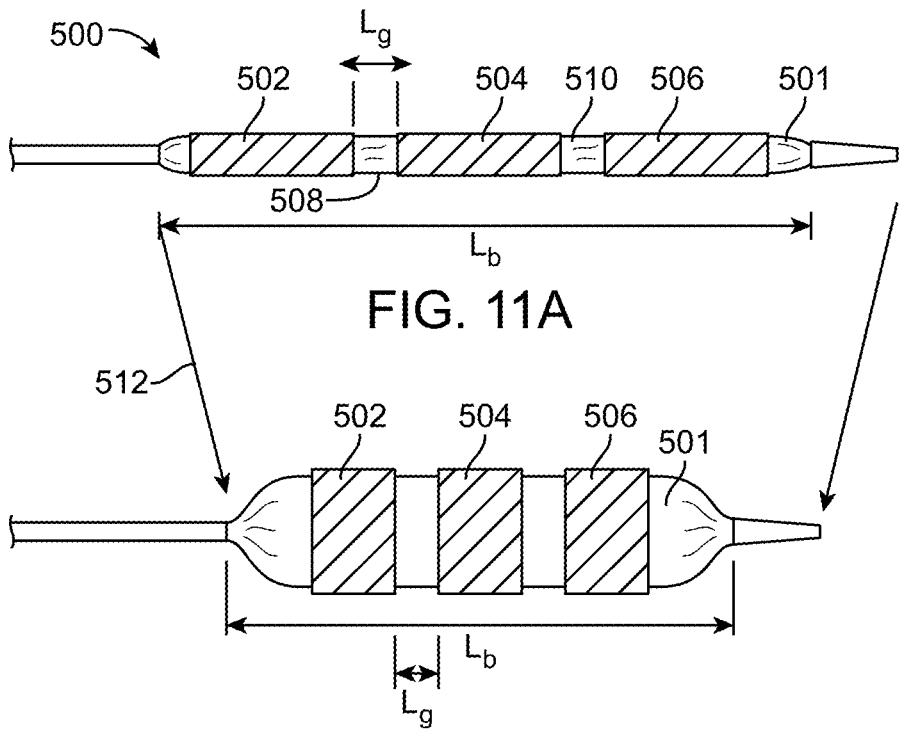
FIG. 11A
FIG. 11B
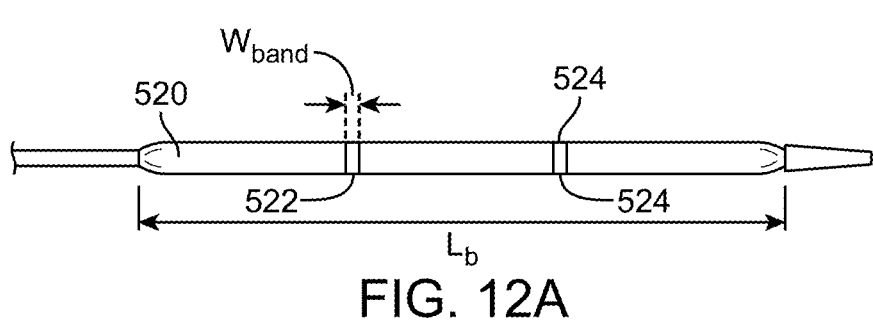
FIG. 12A
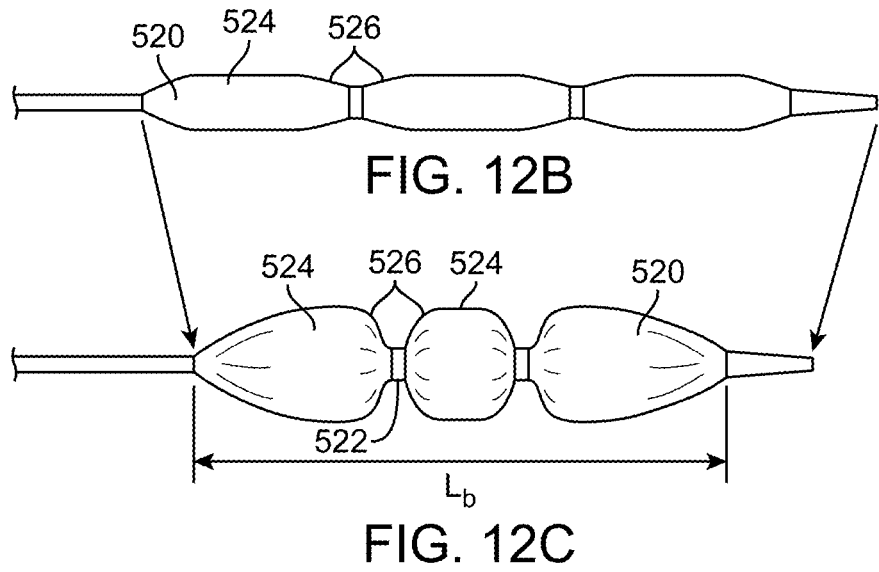
FIG. 12B
FIG. 12C

A-A

SEGMENTED SCAFFOLDS AND DELIVERY THEREOF FOR PERIPHERAL APPLICATIONS

This application is a divisional of U.S. application Ser. No. 13/441,756, filed Apr. 6, 2012, the entire contents of which are hereby incorporated by reference.

BACKGROUND OF THE INVENTION

Field of the Invention

This invention relates to methods of treatment of blood vessels with metallic and polymeric medical devices, in particular, stent scaffolds.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffold or scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of acute closure and restenosis as compared to balloon angioplasty.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. A medicated stent may be fabricated by coating the surface of either a metallic or polymeric scaffold with a bioresorbable polymeric carrier that includes an active or bioactive agent or drug. Polymeric scaffolding may also serve as a carrier of an active agent or drug by incorporating a drug throughout the scaffolding material.

The stent must be able to satisfy a number of mechanical requirements. The stent must have sufficient radial strength so that it is capable of withstanding the structural loads, namely radial compressive forces, imposed on the stent as it supports the walls of a vessel. This structural load will change as a function of time as the vessel heals, undergoes positive remodeling, or adapts to the presence of the stent. Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents implanted in coronary arteries are primarily subjected to radial loads, typically cyclic in nature, which are due to the periodic contraction and expansion of vessels as blood is pumped to and from a beating heart. Stents implanted in peripheral blood vessels, or blood vessels outside the coronary arteries, e.g., iliac, femoral, popliteal, renal and subclavian arteries, however, can undergo significant nonpulsatile forces and must be capable of sustaining both radial forces and crushing or pinching loads. These stent types are implanted in vessels that are closer to the surface of the body, and may be close to joints. Because these stents are close to the surface of the body, they are particularly vulnerable to crushing or pinching loads, which can partially or completely collapse the stent and thereby block fluid flow in the vessel.

The superficial femoral artery (SFA), in particular, can subject a scaffold to various nonpulsatile forces, such as radial compression, torsion, flexion, and axial extension and compression, which place a high demand on the mechanical performance of implants.

Thus, in addition to high radial strength, stents or scaffolds for peripheral vessels such as the SFA, require a high degree of crush recovery. The term "crush recovery" is used to describe how the scaffold recovers from a pinch or crush load, while the term "crush resistance" is used to describe the minimum force required to resist a permanent deformation of a scaffold.

Stents made from biostable or non-bioerodible materials, such as metals, have become the standard of care for percutaneous coronary intervention (PCI) as well as in peripheral applications, such as the superficial femoral artery (SFA), since such stents have been shown to be capable of preventing early and late recoil and restenosis.

However, in many treatment applications, the presence of a stent in a body is necessary for a limited period of time until its intended function of, for example, maintaining vascular patency and/or drug delivery is accomplished. Moreover, it is believed that biodegradable scaffolds allow for improved healing of the anatomical lumen since they allow the vessel to return to its natural state as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold, particularly in peripheral blood vessels, or blood vessels outside the coronary arteries in which a stent is subjected to both radial forces and nonpulsatile forces. Additionally, there are challenges in delivery of polymer scaffolds in peripheral vessels.

SUMMARY OF THE INVENTION

Embodiments of the present invention include a method for delivering a segmented scaffold comprising: providing a delivery balloon comprising a plurality of disconnected scaffold segments arranged end to end and spaced apart by gaps, wherein the segments are crimped to the balloon; and inflating the balloon to radially expand the segments, wherein the relative size of the gaps is constant during and after complete inflation and expansion of the segments.

Embodiments of the present invention include a method for delivering a segmented scaffold comprising: providing a delivery balloon, wherein at least two disconnected scaffold segments are disposed over the balloon and are spaced apart by gaps, wherein each gap comprises a band of raised balloon material; and inflating the balloon to radially expand the segments, wherein the gaps between the segments are maintained to be about a width of the bands of material during and after complete inflation of the balloon and expansion of the segments.

Embodiments of the present invention include a delivery system for a segmented scaffold comprising: a delivery balloon comprising a pre-pillowed band of raised balloon material; and two disconnected scaffold segments crimped over the balloon separated by the band.

Embodiments of the present invention include a method for delivering a segmented scaffold comprising: providing a delivery balloon comprising a plurality of disconnected scaffold segments arranged end to end such that adjacent segments are spaced apart by a gap, wherein the segments are crimped to the balloon; and inflating the balloon to radially expand the segments, wherein the balloon shortens as it is inflated, wherein the shortening of the balloon reduces the increase in the gap between adjacent segments caused by shortening of the segments as they expand Embodiments of the present invention include a delivery system for a segmented scaffold comprising: a delivery balloon comprising a wall including two layers, wherein the layers have different durometer hardness which causes the balloon to shorten when expanded; and two disconnected scaffold segments crimped over the balloon.

Embodiments of the present invention include a delivery system for a segmented scaffold comprising: a delivery balloon; a band wrapped around an axial section of the balloon; and two disconnected scaffold segments crimped over the balloon, wherein the rigid band is in a gap between the two disconnected scaffold segments, wherein when the balloon is inflated the rigid band restricts expansion of the balloon between the scaffold sections which causes shortening of the balloon as it expands.

Embodiments of the present invention include a method for delivering a segmented scaffold comprising: selecting a gap size between implanted disconnected scaffold segments of a segmented scaffold; positioning a first scaffold segment at a first implant site, wherein the first segment is at a reduced crimped diameter; deploying the first segment at the first implant site at an expanded diameter; positioning a second scaffold segment at a second implant site proximal to the deployed first scaffold segment, wherein the second segment is at a reduced crimped diameter; and deploying the second segment at an expanded diameter, wherein a gap between the deployed first scaffold segment and deployed second segment is the selected gap size.

Embodiments of the present invention include a system for deploying a segmented scaffold comprising: a sheath comprising an inner lumen and distal end with an opening; a delivery balloon disposed within the lumen; a first scaffold segment and a second scaffold segment arranged end to end, wherein the first segment is distal to the second segment and is crimped over a balloon, wherein the balloon and segments are movable along the cylindrical axis of the lumen.

Embodiments of the present invention include a method of delivering a segmented scaffold comprising: selecting a gap size between implanted disconnected scaffold segments of a segmented scaffold; positioning a sheath proximal to implant sites, wherein a first scaffold segment and a second scaffold segment crimped over a balloon are disposed within the sheath, wherein the first segment is distal to the second segment; extending the first segment out of the sheath; deploying the first segment at a first implant site; after deployment of the first segment, positioning the second segment out of the sheath; and deploying the second segment at the second implant site, wherein a gap between the deployed first segment and the deployed second segment is the selected gap size.

Embodiments of the present invention include a method of delivering a segmented scaffold comprising: selecting a gap size between implanted scaffold segments of a segmented scaffold; positioning a sheath distal to implant sites, wherein at least a second scaffold segment is disposed within the sheath, wherein a first scaffold segment is distal to the second segment and is crimped over a balloon; deploying the first segment at a first implant site; positioning the balloon within the second segment; securing the second segment over the balloon; extending the second segment out of the sheath to a second implant site proximal to the deployed first segment; and deploying the second segment at the second implant site, wherein a gap between the deployed first segment and the deployed second segment is the selected gap size.

Embodiments of the present invention include a method of delivering a segmented scaffold comprising: positioning a sheath proximal to implant sites, wherein three or more scaffold segments crimped over a balloon are disposed within the sheath; extending a set of at least two of the segments out of the sheath, wherein at least at least one segment remains within the sheath; deploying the set of segments at a set of implant sites; after deployment of the set of segments, positioning an additional segment remaining in the sheath outside of the sheath; and deploying the additional segment at a second implant site, wherein a gap between the proximal-most set of deployed segments and the deployed additional segment is a selected gap size.

Embodiments of the present invention include a method of delivering a segmented scaffold comprising: providing a delivery balloon, wherein two disconnected scaffold segments are disposed over the balloon and are spaced apart by a gap, inflating the balloon to radially expand the segments, wherein a width of the gap between the segments is constant during and after complete inflation of the balloon and expansion of the segments.

Embodiments of the present invention include a method of delivering a segmented scaffold comprising: providing a delivery balloon, wherein two disconnected scaffold segments arranged end to end and spaced apart by a gap are disposed over the balloon, wherein the segments are crimped to the balloon; inflating and expanding the balloon to expand the segments, wherein expansion of the segments increases the width of the gap between the segments; and applying an axially directed force to the balloon to shorten the balloon to reduce the width of the gap.

Embodiments of the present invention include a system for deployment of a segmented scaffold comprising: an outer tubular member; an inner elongate member disposed within the outer tubular member; and a delivery balloon disposed over at least the inner elongate member, wherein a proximal end of the balloon is attached to the outer tubular member and a distal end of the balloon is attached to a distal end of the inner elongate member, wherein the inner elongate member is axially slideable within the outer tubular member, wherein when the balloon is at least partially inflated, sliding the inner elongate member proximally causes the balloon to shorten.

Embodiments of the present invention include a system for deployment of a segmented scaffold comprising: a delivery balloon; a first scaffold segment and second scaffold segment arranged end to end and crimped over the balloon; at least one spacer member attached to the balloon in a gap between the segments, wherein the at least one spacer member is associated with each of the segments in a manner that maintains a constant gap size between the segments when the balloon inflates and expands the segments.

Embodiments of the present invention include a method for deployment of a segmented scaffold comprising: a delivery balloon and a first scaffold segment and second scaffold segment arranged end to end and crimped over the balloon; inflating the balloon to expand the first and second segments, wherein at least one spacer member attached to the balloon and associated with the segments maintains a constant gap size between the segments when the balloon inflates and expands the segments.

Embodiments of the present invention include a method for delivering a segmented scaffold comprising: positioning a delivery balloon comprising a plurality of disconnected scaffold segments arranged end to end and spaced apart by gaps at a treatment site within a blood vessel of a patient, wherein the segments are crimped to the balloon, wherein a surface of the balloon between the gaps comprises a coating including a therapeutic agent; and inflating the balloon to radially expand and implant the segments at the implant site, wherein the therapeutic agents reduces restenosis at the implant site at or proximal to the gaps.

Embodiments of the present invention include a system for delivering a segmented scaffold comprising: a delivery balloon; and a plurality of disconnected scaffold segments arranged end to end and spaced apart by gaps which are crimped over the balloon, wherein a surface of the balloon between the gaps comprises a coating including an antiproliferative therapeutic agent.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 10A depicts an assembly including scaffold segments positioned over a stepped mandrel prior to disposing into a pre-crimper.

FIG. 10B depicts the assembly in FIG. 10A after the scaffold segments are pre-crimped.

FIG. 11A depicts a balloon assembly with a balloon in a deflated state.

FIG. 11B depicts the balloon assembly of FIG. 11A with the balloon in an inflated state.

FIG. 12A depicts a delivery balloon in a deflated state with a band disposed around the balloon at two axial positions.

FIG. 12B depicts the balloon of FIG. 12A in a partially inflated state.

FIG. 12C depicts the balloon of FIG. 12A in a fully inflated state.

DETAILED DESCRIPTION OF THE INVENTION

Coronary arteries refer generally to arteries that branch off the aorta to supply the heart muscle with oxygenated blood. Peripheral arteries refer generally to blood vessels outside the heart. In both coronary artery disease and peripheral artery disease, the arteries become hardened and narrowed or stenotic and restrict blood flow. In the case of the coronary arteries, blood flow is restricted to the heart, while in the peripheral arteries blood flow is restricted leading to the kidneys, stomach, arms, legs, feet, and brain. The narrowing is caused by the buildup of cholesterol and other material, called plaque, on their inner walls of the vessel. Such narrowed or stenotic portions are often referred to as lesions. Arterial disease also includes the reoccurrence of stenosis or restenosis that occurs after an angioplasty treatment. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

A stent, a stent scaffold, or scaffold includes a plurality of cylindrical rings connected or coupled with linking elements. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts primarily serve to maintain stability and connectivity between the rings. For example, a stent may include a scaffold composed of a pattern or network of interconnecting structural elements or struts.

Figure 1:
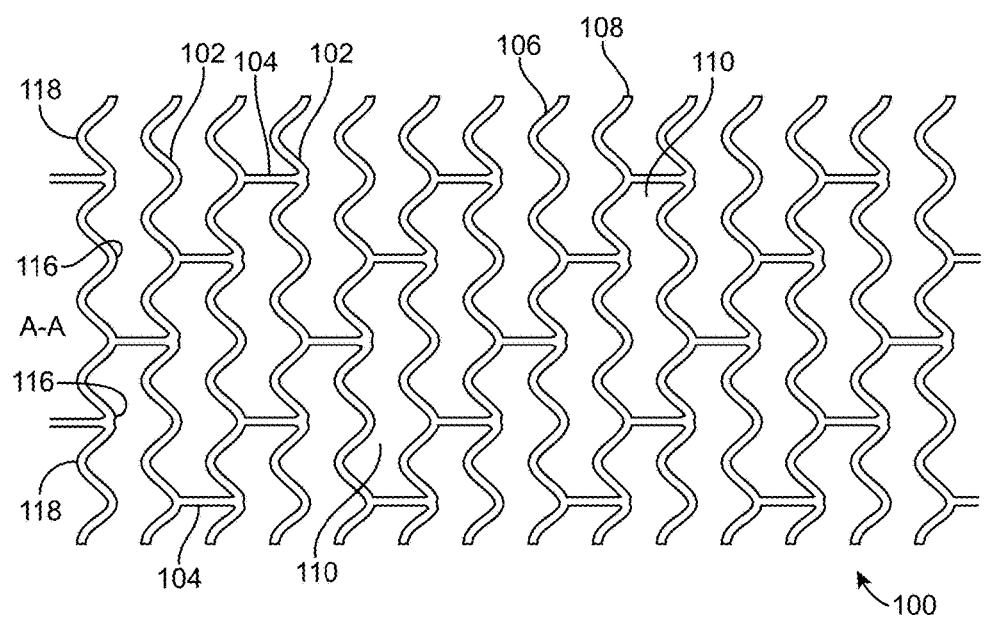
FIG. 1 depicts an exemplary stent scaffold.

FIG. 1 illustrates a portion of an exemplary prior art stent or scaffold pattern 100 shown in a flattened view. The pattern 100 of FIG. 1 represents a tubular scaffold structure so that an axis A-A is parallel to the central or longitudinal axis of the scaffold. FIG. 1 shows the scaffold in a state prior to crimping or after deployment. Pattern 100 is composed of a plurality of ring struts 102 and link struts 104. The ring struts 102 form a plurality of cylindrical rings, for example, rings 106 and 108, arranged about the cylindrical axis A-A. The rings have an undulating or sinusoidal structure with alternating crests or peaks 116 and troughs or valleys 118. The rings are connected by the link struts 104. The scaffold has an open framework of struts and links that define a generally tubular body with gaps 110 in the body defined by rings and struts. A cylindrical tube may be formed into this open framework of struts and links by a laser cutting device that cuts such a pattern into a thin-walled tube that may initially have no gaps in the tube wall.

The structural pattern in FIG. 1 is merely exemplary and serves to illustrate the basic structure and features of a stent or scaffold pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped onto a balloon or catheter for delivery into a bodily lumen.

The width and or thickness of the struts in a scaffold may be 80 to 300 microns, or more narrowly, 100 to 250 microns, 140 to 180 microns, or 140 to 160 microns Semicrystalline polymers such as poly(L-lactide) (PLLA) with glass transition temperature (Tg) above human body temperature may be suitable as materials for a totally bioresorbable scaffold since they are relatively stiff and strong at the conditions of the human body. However, they tend to be brittle at these conditions. These polymer systems exhibit a brittle fracture mechanism in which there is little plastic deformation prior to failure. As a result, a stent fabricated from such polymers can be vulnerable to fracture during use of a scaffold, i.e., crimping, delivery, deployment, and during a desired treatment period post-implantation.

Embodiments of the present invention are applicable to endovascular treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures formed from tubes, wire structures, and woven mesh structures.

In general, the initial clinical needs for a bioresorbable scaffold is to provide mechanical/structural support to maintain patency or keep a vessel open at or near the deployment diameter. The scaffold is designed to have sufficient radial strength or vessel wall support for a period of time. The vessel wall support provided by the stent allows the stented segment of the vessel to undergo healing and remodeling at the increased diameter. Remodeling refers generally to structural changes in the vessel wall that enhance its load-bearing ability.

A period of vessel wall support is required in order to obtain permanent positive remodeling and vessel healing and hence maintenance of vessel patency. As the polymer of the stent degrades, the radial strength of the scaffold decreases and the load of the vessel is gradually transferred from the scaffold to the remodeled vessel wall. In addition to the decline in radial strength, the degradation of the scaffold also causes a gradual decline in the mechanical integrity, i.e., connectivity of struts and the size and shape of the overall scaffold structure. The struts gradually resorb and disappear from the vessel.

The amount of movement experienced by a peripheral scaffold in the peripheral artery is greater than what a coronary scaffold experiences in the coronary artery. A peripheral scaffold can be subjected to a high degree of flexing, axial elongation/compression, pinching, bending, and torsion after implantation. Axial stresses on the scaffold can arise from the axial compression and extension, flexural stresses are imposed by lateral flexing, crushing forces are imparted by pinching, while helical stress can arise from torsional forces.

Such stresses are propagated along the length of the scaffold and can impart significant forces throughout the scaffold structure. The forces can cause failure in ring struts, resulting in a decrease or loss in vessel wall support provided by the scaffold. Such forces can be transmitted along the length of the scaffold by link struts that connect rings.

Link strut breakage is not inherently deleterious to either performance or safety. Bench testing and animal study results suggest that scaffold properties of radial strength, crush recovery, and crush resistance are primarily attributable to the mechanical/structural integrity of the rings in the scaffold and not the links.

Strut breakage can lead to release of fragments in the blood and tissue irritation from broken strut fragments. Fragment release could result in thrombosis. Broken fragments can be mechanically injurious to the vessel leading to tissue irritation or even vessel dissection and perforation.

Figure 2:
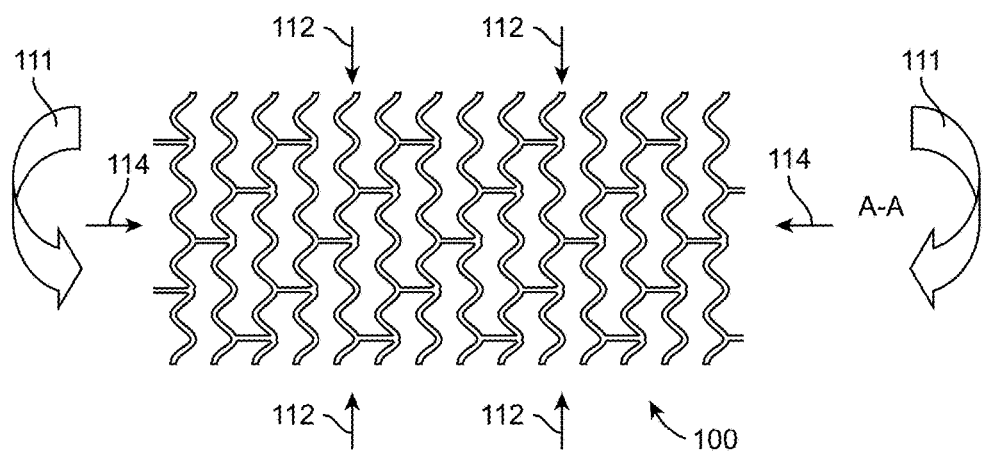
FIG. 2 depicts an exemplary scaffold pattern which shows schematically the forces acting on the scaffold.

FIG. 2 depicts the exemplary scaffold pattern 100 which shows schematically the forces acting on the peripheral scaffold. Line A-A represents the cylindrical axis of the stent. The arrows around the edges represent the forces acting on the scaffold during delivery and after deployment. Arrows 111 represent bending, arrows 112 represent radial compression, and arrows 114 represent axial compression. Bending occurs during delivery through torturous anatomy and after deployment.

Radially compressive forces on the scaffold are caused by the push back of the vessel walls on the scaffold. Axial compressive forces in the SFA arise due to movement of a leg such as during walking or bending of the leg. In the SFA, the axial compressive forces can be considerable as the vessel is compressed up to 7% or more and relaxed repeatedly up to one million cycles/year.

Cracks in the scaffold occur when it is subjected to a sufficiently high force such as resulting from bending during delivery or repetitive forces after deployment that cause fatigue. These cracks can cause a loss of radial strength or separation of struts of the scaffold that drift downstream of the scaffold.

A crack in the ring strut may cause a reduction or loss of radial strength, while a crack in the link is less damaging to the scaffold in terms of radial strength, crush resistance, and crush recovery. It is believed that if the axial forces on the scaffold were reduced, the occurrence of ring cracks would be significantly reduced. When axial forces through the links to the ring struts are reduced, then the potential for ring strut fractures are also reduced.

The various embodiments of the present invention are directed to peripheral scaffolds that are subjected to significant nonpulsatile forces upon implantation. Embodiments are further directed to methods and systems for delivering such peripheral scaffolds. The embodiments of the scaffold designs are directed to reducing or eliminated strut fracture and breakage during use of the scaffold.

Various embodiments include a scaffold composed of axial scaffold segments that are not connected by link struts. Embodiments of such a scaffold include two or more radially expandable axial scaffold segments arranged axially end to end. The axial segments, in particular, axially adjacent segments are not connected by any physical structure or material of the scaffold. The axial segments, however, may be indirectly in contact through another structure such as a support member or a sheath. The axial segments may further be connected by structures not part of structure from which the scaffold segments are formed, such as a tube.

In general, upon deployment of the scaffold segments, forces subjected on one axial segment cannot be transmitted to other axial segments through linking struts as such forces are by linking struts of a scaffold shown in FIG. 1. The axial segments may be composed of a plurality of interconnected struts. Forces subjected to a segment can be transmitted between struts within the segment, but not between segments.

In some embodiments, the axial segments are composed of one or more cylindrical rings of struts. A cylindrical ring may be composed of undulating struts having crests and troughs. The cylindrical rings of struts that are adjacent in a segment are connected. The rings may be connected by link struts. Alternatively, the rings may be directly connected to one another without link struts. The number of rings in a segment may be one or any number greater than one. In some embodiments, a segment can have 1 or more, 2 or more, 1 to 6 rings, 1 to 3 rings, 2 to 6 rings, or 2 or 3 rings.

Upon deployment, the axial segments remain intact for a period of time and maintain a ring shape at or near the deployed diameter. Since the axial segments are not connected, they are uncoupled which prevents transmission of axial compression between segments. The decoupled axial segments retain sufficient radial strength to support the vessel at or near the deployed diameter. The decoupling of the axial segments reduces stress, for example, from axial compression that causes fracture of ring struts. The reduced ring strut fracture helps maintain the radial strength and the crush recovery and resistance to broken off struts of the scaffold floating down the vessel as emboli. The decoupling of rings reduces or prevents propagation of fracture of rings due to bending of the scaffold structure along its axis.

In some embodiments, a scaffold with disconnected axial segments can be fabricated by forming the axial segments separately. For example, a scaffold pattern can be cut into a thin-walled tube having an axial length the same as the desired axial segment. Alternatively, a scaffold can be fabricated by laser cutting a tube and then axial segments can be formed cutting the scaffold into disconnected axial segments by cutting link struts between segments or cutting the link struts between segments off entirely. Unless otherwise specified, scaffold segments or segments refer to disconnected scaffold segments or segments.

The stability of an axial segment may depend on the length of the axial segment. The stability is inversely related to the length of the axial section. The susceptibility to fracture from nonpulsatile forces, however, is directly related to the length of the axial section. The length of the axial segments should be large enough so that it has a desired stability, while having reduced fracture arising from nonpulsatile forces.

The radial strength and radial stiffness of a scaffold or scaffold segment increases with the degree of connectivity of a scaffold. The degree of connectivity refers in part to the number of link struts between rings and the length of the link struts: more link struts and shorter link struts tend to increase strength and stiffness. The stiffer the scaffold, the more susceptible the scaffold is to fracture. In the present embodiments, since compressive forces are not transmitted along an entire scaffold length, the scaffold segments can be made with a higher connectivity than a scaffold that does not have disconnected axial segments.

In the scaffolds such as the one depicted in FIG. 1, the crests of the axial rings are axially aligned or approximately axially aligned. The stiffness of the axial segments of such a scaffold can be increased by increasing the number of link struts between axially adjacent peaks of adjacent rings. Every pair of aligned peaks between adjacent rings can be connected, every other pair of aligned peaks can be connected, or every third pair of aligned peaks can be connected by a link strut.

In some embodiments, the axial segments may be composed of rings arranged such that the crests in one ring are axially aligned or almost axially aligned with the troughs in an adjacent ring. The rings are connected by at least one link strut between an aligned crest and trough. Stiffness is greatest with a link strut between each aligned crest and trough. Greater flexibility is introduced by having fewer than every aligned crest and trough connected by a link strut. For example, only every other aligned crest and trough can be connected, or only every third aligned crest and trough can be connected by a link strut. Additionally, the length of the link struts in the axial segments can be adjusted to modify the stiffness of the axial segment. Decreasing the length of the links increases both the radial strength and radial stiffness of the axial segment since the number of rings per segment length is maximized. Such a pattern may also be described as a plurality of rings composed of diamond-shaped elements formed of struts. The elements of the rings are connected at circumferentially aligned vertices of the diamond-shaped elements. Axially adjacent rings are connected at axially aligned vertices either by a short link strut or at the intersection of vertices of elements of adjacent rings.

Figure 3A:
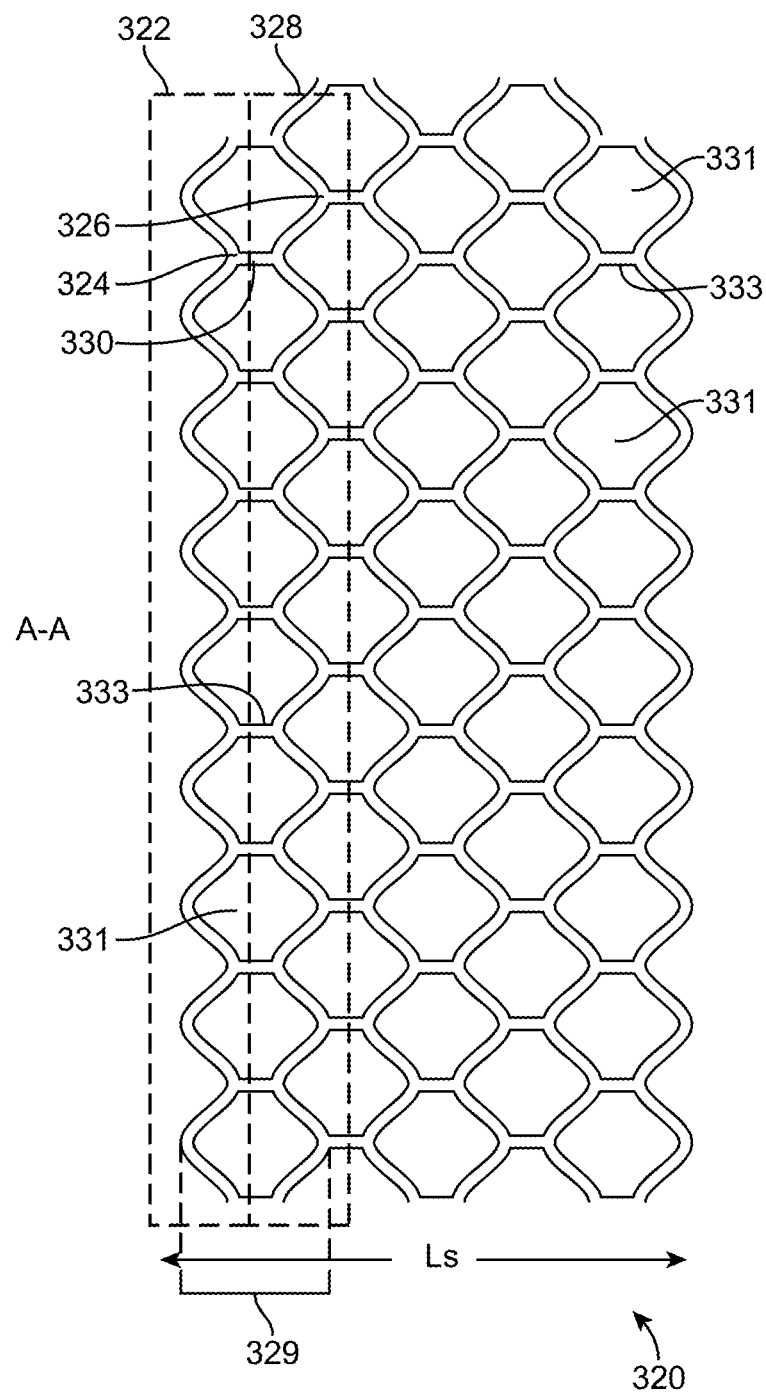
FIG. 3A depicts an exemplary scaffold segment of a segmented scaffold.

FIG. 3A depicts an exemplary axial segment 320 viewed in a flattened configuration composed of a plurality of rings of undulating struts with crests and troughs. Line A-A is the longitudinal axis of the axial segment. An exemplary ring 322 has crests 324 and troughs 326. As shown in FIG. 3A, every crest in ring 322 is connected to every trough in adjacent ring 328 by a short link strut 330. The arrangement of rings 322 and rings 328 forms a plurality of rings 329 of diamond-shaped elements 331 formed of struts. The diamond-shaped elements 331 of the rings are connected at circumferentially aligned vertices of the diamond-shaped elements.

Ls is the length of the axial segment. Ls may be 3 to 6 mm, 6 to 8 mm, 8 to 10 mm, 10 to 12 mm, or greater than 12 mm in an as cut or as fabricated configuration. Ls increases when the segment is crimped to a decreased diameter and then decreases when expanded from a crimped configuration. Length change is affected by the number of peaks in a ring and the width of the diamonds. The length change (increases or decreases) with the number of peaks and (increases or decreases) with the width of the diamonds.

Figure 3B:
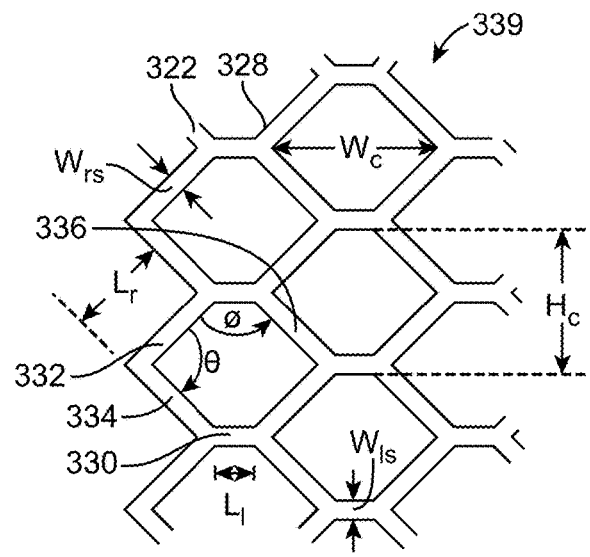
FIG. 3B depicts a close-up view of a portion of the scaffold segment in FIG. 3A illustrating various features.

FIG. 3B depicts a close-up view of a portion 339 of axial segment 320 illustrating various features. As shown in FIG. 3B, Lr is the length of a ring strut, for example, strut 332 between a crest and trough in a ring and Wrs is the width of the ring strut. Ll is the length of short link strut 330 that connects crests and troughs of adjacent rings and Wls is the width of the link strut. $\theta$ is the angle at the longitudinal vertex of the diamond shaped cells, i.e., between struts 332 and 334 in a ring that intersects at a crest or trough. $\varphi$ is the angle between struts 332 and 336 which are joined by short link strut 330 and a diamond-shaped cell. Hc is the height of the diamond-shaped cell and Wc is the width of the diamond-shaped cell.

$\theta$ may be 90 degrees, 90 to 95 degrees, 95 to 100 degrees, 100 to 110 degrees, or greater than 110 degrees. $\theta$ may be 90 degrees, 85 to 90 degrees, 80 to 85 degrees, 70 to 80 degrees, or less than 70 degrees. $\varphi$ may be 90 degrees, 85 to 90 degrees, 80 to 85 degrees, 70 to 80 degrees, or less than 70 degrees. $\varphi$ may be 90 degrees, 90 to 95 degrees, 95 to 100 degrees, 100 to 110 degrees, or greater than 110 degrees.

Exemplary values for $\theta$ and $\varphi$ are about 70 and 110 degrees, respectively. Values in this range tend to reduce segment shortening from crimping to deployment. Other exemplary values for $\theta$ and $\varphi$ are about 110 and 70 degrees, respectively. Values in this range tend to increase segment's radial strength and crush resistance.

The segments can include radiopaque marker embedded within holes in the scaffold segment to aid in visualization of the implanted scaffold. In some embodiments, the markers are embedded in holes in the short link struts 330 of FIG. 3A. In other embodiments, the markers are embedded in holes in ring struts 332 of FIG. 3B.

When a scaffold segment is crimped, the Ls increases which is caused by bending at the vertices of the diamond-shaped elements. Specifically, when the scaffold segment is crimped, $\theta$ decreases and $\varphi$ increases. When a scaffold segment is deployed, the Ls shortens which is caused by bending at the vertices of the diamond-shaped elements corresponding to an increase in $\theta$ and a decrease in $\varphi$.

The segment properties of radial strength and stiffness can be modified through adjustment of the as-cut geometrical parameters of the diamond-shaped elements. For example, radial strength and stiffness is increased by increasing Hc which results in a decrease in Wc and also corresponds to a decrease in $\varphi$ and an increase in $\theta$.

In some segment design embodiments, the diamond-shaped elements are square-shape or approximately square-shaped in the as-cut condition. In such embodiments, $\varphi$ is the same or approximately the same as $\theta$. For example, ABS ($\varphi-\theta$) may be 2 or about 2 degrees or less than 2 degrees.

In other segment design embodiments, the diamond-shaped elements can be taller or greater in the circumferential direction or, Hc>Wc and φ>θ. In such embodiments, the θ−φ may be greater than 2 degrees, 2 to 4 degrees, 4 to 8 degrees, greater than 8, about 3 degrees, about 4 degrees, or about 5 degrees.

$L_l$ may be less than 10% or 10% to 20%, 20% to 30%, 30 to 40%, or greater than 40% of a ring strut length between a crest and a trough. Exemplary link struts may have a length of less than 0.01 in, 0.01 to 0.02 in, 0.02 to 0.04 in, 0.04 to 0.06 in, or greater than 0.06 in. In some embodiments, adjacent rings are connected at an intersection of the opposing crests and troughs such that a length of the link strut is effectively the width of the intersection.

Figure 4:
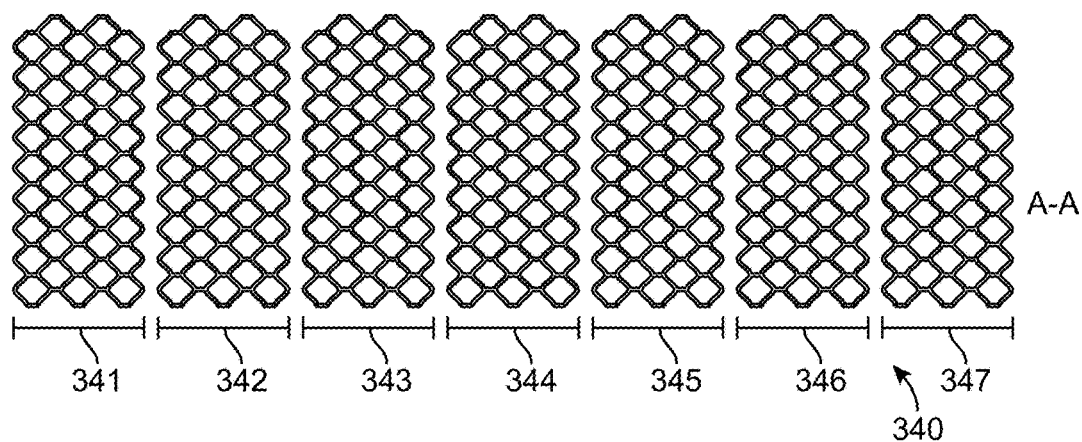
FIG. 4 depicts a segmented scaffold composed of a plurality of axial segments from FIG. 3A.

FIG. 4 depicts a segmented scaffold 340 composed of a plurality of axial segments 341 to 347, from FIG. 3A. The delivery of a scaffold composed of decoupled or disconnected axial segments can be achieved by disposing the axial segments over a catheter of delivery balloon. The axial segments can be arranged end to end and spaced apart on a single balloon or multiple balloons arrange end to end. The axial segments may be crimped over the balloon to a reduced diameter configuration to allow for delivery of a vascular system to a treatment site.

Generally, stent crimping is the act of affixing a radially expandable scaffold or stent to a delivery catheter or delivery balloon so that it remains affixed to the catheter or delivery balloon until the physician desires to deliver the stent at the treatment site. Delivery balloons may be compliant, semi-compliant, or noncompliant and are made from PEBAX, nylon, or other type of common balloon material. Examples of such crimping technology which are known by one of ordinary skill in the art include a roll crimper; a collet crimper; and an iris or sliding-wedge crimper. In the sliding wedge or iris crimper, for example, adjacent pie-piece-shaped sections move inward and twist toward a scaffold in a cavity formed by the sections, much like the leaves in a camera aperture.

Figure 5:
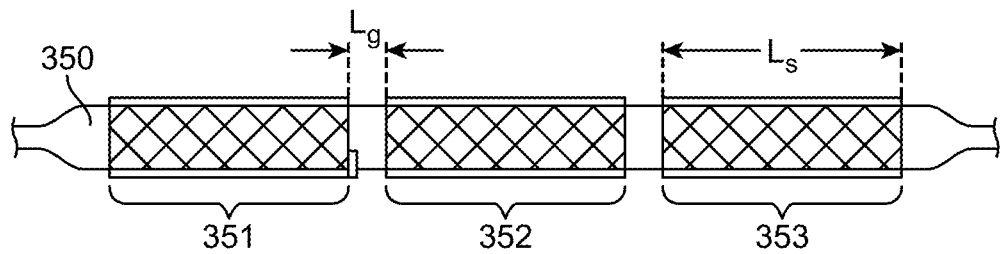
FIG. 5 depicts scaffold segments of a segmented scaffold mounted over a balloon in a folded configuration.

FIG. 5 depicts a projection of axial segments 351, 352, and 353 disposed over a balloon 350 in a deflated configuration. Axial segments are crimped tightly over the balloon in a reduced diameter configuration. A crimped configuration generally may correspond to the inner surface of the segments in contact with the outer surface of a balloon. The axial segments are spaced apart by a distance, size, or width Lg, which is the gap between segments. Lg can change during inflation and deployment of the segments to a deployed diameter due to movement of the segments and axial contraction or shortening of the segments. Lg at deployment should be large enough to avoid interference or contact of the segment ends during bodily movements. Lg at deployment should be large enough so that there is axial stability and the support of the vessel is continuous. In exemplary embodiments, the segments when deployed are spaced apart by 0.5 to 2 mm, or more narrowly, 0.5 to 1 mm, 1 to 2 mm, 2 to 3 mm. The required Lg is determined by the anatomy that the segmented scaffold will be deployed in to, i.e., in the SFA it will need to be greater than for the Iliac where vessel compression and bending are virtually zero. In general, Lg is higher for anatomies with higher vessel compression and bending.

Factors that influence a desired Lg at deployment include the axial compression in the vessel, bending of the vessel, and stability in presence of side branches coming off of a segment of the vessel where the scaffold is implanted.

When compressive loads are placed on the scaffold the axial compression may occur predominantly between segments. Generally, it is important to allow for the decrease in the spacing of the segments during compression and loading. Therefore, Lg at deployment should be large enough so that the segments do not contact or interfere with each other during axial compression. The Lg at deployment can be selected to allow for an axial compression of 7 to 15%, or for example, about 13%.

The bending of a vessel with implanted segments results in a decrease in the Lg at the concave or inner side of the bend with the gap widening toward the convex or outer side of the bend. The segments at the inner side of the bend can interfere or make contact with each other if the initial gap is not wide enough. The Lg at deployment can be selected to allow for bending of 20 to 30 degrees or less than 30 degrees, or about 30 degrees. In this case, a 3 mm gap reduces to 0.8 mm at the inner side of the gap.

The scaffold segments may be deployed in a vessel that includes a side branch and a gap between segments that overlap this side branch. In this case, Lg can be the width of the side branch or greater or less than the width of the side branch. To maintain axial stability of a segment of a segmented scaffold over a side branch, the length of a segment needs to be longer that the side branch so that the radially supported length of the segment is typically 1.5 times the segment diameter when deployed. This diameter:length ratio can be less than a 1:1 ratio, a 1:1 ratio, a 1:1.5 ratio or a 1:2 ratio or greater. The ratio is dependant among other things on the size of the nonpulsatile forces at the delivery site. For example, the Lg at deployment can be less than 2 or 3 mm.

The diamond pattern disclosed herein tends to maximize the relative friction between the vessel wall and the segments. With this and the high radial and axial rigidity of the diamond pattern, endothelialization of the segments may be sped up and vessel irritation may be reduced. With quick endothelialization, the scaffold/vessel wall becomes a composite structure which in itself enhances the radial strength and hence crush resistance. With most, if not all of the movement transferred to the gaps between the segments, the design utilizes the natural flexibility of the vessel walls to handle any compression, bending and torsional movements.

In some embodiments, a single high radial strength and stiff scaffold segment, such as described above, may be implanted at an implant site. Implanting a single segment without additional segments may be useful in treatments involving vessels that do not undergo axial compression, torsion, or bending. Examples include the Iliac and Renal artery.

Figure 6A:
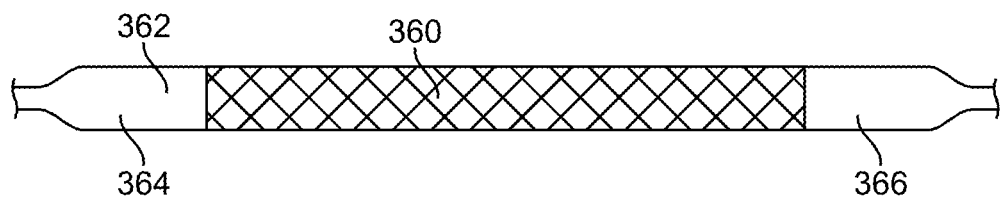
FIG. 6A depicts a schematic view of a scaffold crimped over a balloon prior to inflation.
Figure 6B:
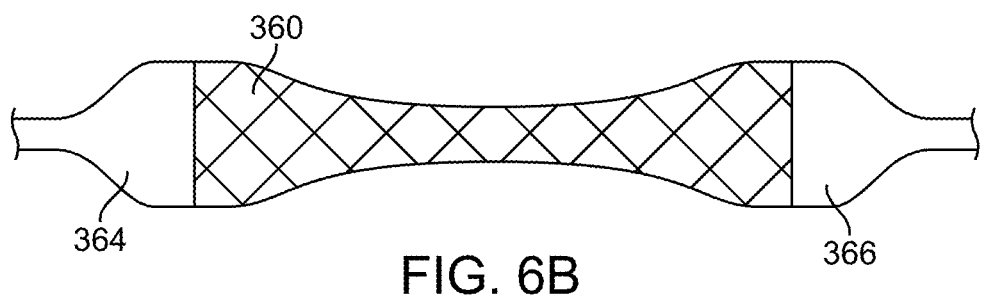
FIG. 6B shows the scaffold and balloon of FIG. 6A when the balloon is partially inflated.
Figure 6C:
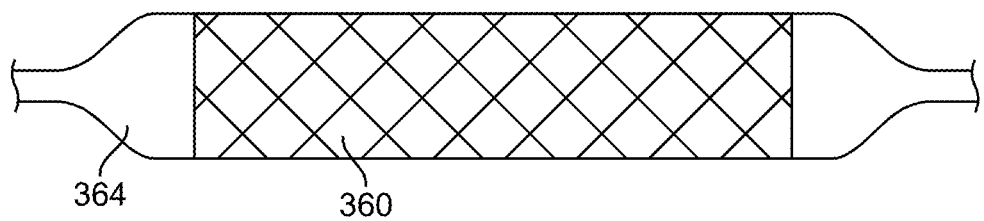
FIG. 6C depicts the scaffold and balloon of FIGS. 6A-B when balloon is fully inflated and expanded.

During deployment at a lesion site of a conventional balloon expandable stent or scaffold, the balloons generally start to expand at the proximal and distal ends first, producing a dog bone shape. As pressure is increased, the balloon expands in the center, expanding the scaffold in the center also. This is illustrated in FIGS. 6A-C. FIG. 6A depicts a schematic view of a stent 360 crimped over a balloon 362 prior to inflation. FIG. 6B shows that as the balloon inflates, proximal end 364 and distal end 366 expand first, with a center section between the ends expanded less or not expanded. FIG. 6C depicts a fully expanded balloon with the center section expanded as well.

With the segmented scaffold which can include several short scaffolds on a single balloon, the balloon can expand in a similar manner, i.e., expanding at the proximal and distal ends first, followed by expansion of a center section. Expansion at the ends first has the tendency to push the segments axially towards the center of the balloon which decreases the segment to segment gap. The gap may be decreased to the point that the segments collide with each other. This movement of the individual segments axially along the balloon during deployment, therefore, can change the segment to segment gap to an undesirably small size which can result in interference of the segments. Additionally, the segment to segment spacing will not necessarily be the same between all segments. A reduced gap or zero gap may be acceptable where nonpulsatile forces are virtually zero.

Embodiments of the present invention include delivery systems and methods that maintain a segment to segment gap between axial segments expanded by a balloon that is consistent during and after complete inflation of the balloon and expansion of the segments. In some embodiments, the gap sizes between all or some of the segments change during inflation, however, some of the gaps have the same width even as their widths change during and after complete inflation and expansion of the segments. In other embodiments, some gap sizes are different; however, the relative size of gaps is constant as their widths change during and after complete inflation and expansion of the segments.

An aspect of these embodiments is a delivery balloon that maintains the consistent segment to segment gap size between some or all of the segments during balloon inflation. Embodiments of the balloon include a delivery balloon including one or more sections or bands of raised or pre-pillowed balloon material around the circumference of the balloon. The raised or pre-pillowed sections of the balloon have an axial width corresponding to a desired initial segment to segment gap size. The segments are crimped over the balloon such that a pre-pillowed section is in a gap between adjacent segments. The distal end of one segment is separated from the proximal end of the adjacent segment by an axial distance equal to or slightly greater than the width of the pre-pillowed section. Pillowed sections in the balloon can also be located adjacent to the proximal end of a proximal-most segment at the proximal end of the balloon and adjacent to the distal end of a distal-most segment at the distal end of the balloon.

In some embodiments, each of the pre-pillowed sections or some of the pre-pillowed sections can have the same axial width. As the balloon inflates and expands the segments, the gap between adjacent segments is the width of the pillowed sections between these segments. As the balloon inflates and expands the segments, the gaps between segments separated by the pre-pillowed sections remain the same.

In other embodiments, some of the pillowed sections can have different axial widths. As the balloon inflates and expands the segments, the relative gap size of gaps between segments separated by pillowed sections that have the different widths remains the same. Thus, even though the gap sizes change during inflation, the relative gap sizes remain consistent during inflation and expansion of the segments.

Figure 7:
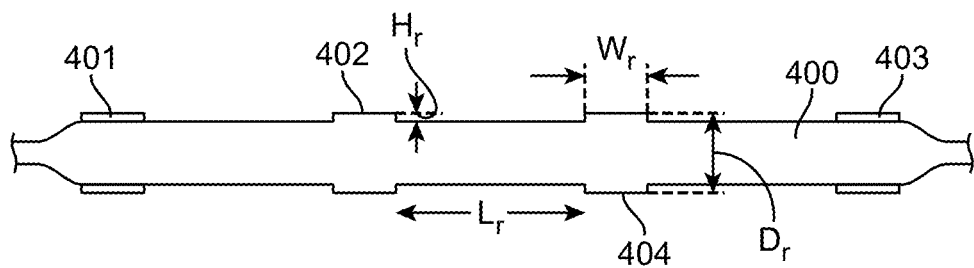
FIG. 7 depicts an axial projection of an exemplary delivery balloon in a deflated configuration including pre-pillowed bands of balloon material.

FIG. 7 depicts an axial projection of an exemplary delivery balloon 400 in a deflated configuration including pre-pillowed sections 401, 402, 403, and 404. Pre-pillowed sections 401, 402, 403 and 404 are bands of raised balloon material around the circumference of balloon 400. Pre-pillowed sections 401, 402, 403, and 404 have a width Wr. Pre-pillowed sections 401, 402, 403, and 404 have an outside diameter Dr and a distance Hr above the surface of the unpre-pillowed surface of the balloon. Pre-pillowed sections 401/402, 402/404, and 404/403 are separated by a distance Lr.

Figure 8A:
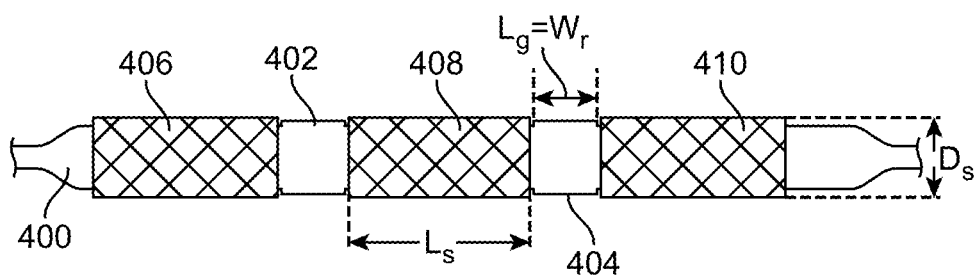
FIG. 8A depicts a balloon in a folded condition with three scaffold segments crimped over the balloon.

FIG. 8A depicts balloon 400 in a deflated condition over which three axial scaffold segments 406, 408, and 410 are crimped. Each segment has a length, Ls and outer diameter Ds. Pre-pillowed section 402 is between segment 406 and segment 408. Pre-pillowed section 404 is between segment 408 and segment 410. The segment to segment gap distance, Lg, between segments 406/408 and segments 408/410 are equal to the width Wr of the pre-pillowed sections 402 and 404, respectively. Thus, the distal end of segment 406 abuts against the proximal end of pre-pillowed section 402 and the proximal end of segment 408 abuts against the distal end of pre-pillowed section 402. Also, the distal end of segment 408 abuts against the proximal end of pre-pillowed section 404 and the proximal end of segment 410 abuts against the distal end of pre-pillowed section 404. Also, the proximal end of segment 406 abuts against the distal end of pre-pillowed section 401 and the distal end of segment 410 abuts against the proximal end of pre-pillowed section 403.

The outer diameter Ds of the segments is greater than the outside diameter Dr of the pre-pillowed sections. Ds may be 1 to 5%, 5-10%, or greater than 10% more than Dr. Ds may also be the same as or about the same as Dr.

Figure 8B:
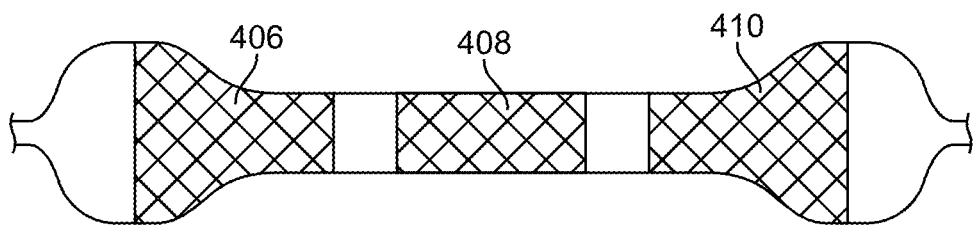
FIG. 8B depicts the balloon-scaffold assembly of FIG. 8A when balloon is in a partially inflated state.

FIG. 8B depicts the balloon-scaffold assembly of FIG. 8A when balloon 400 is in a partially inflated state. As shown in FIG. 8B, the proximal portion and distal portions of balloon 400 are inflated first and a center portion is not inflated. The inflation of the proximal and distal portions of balloon 400 expands a proximal section of segment 406 and a distal section of segment 410. A distal section of segment 406, proximal section of segment 410 and segment 408 remain in a crimped state.

Figure 8C:
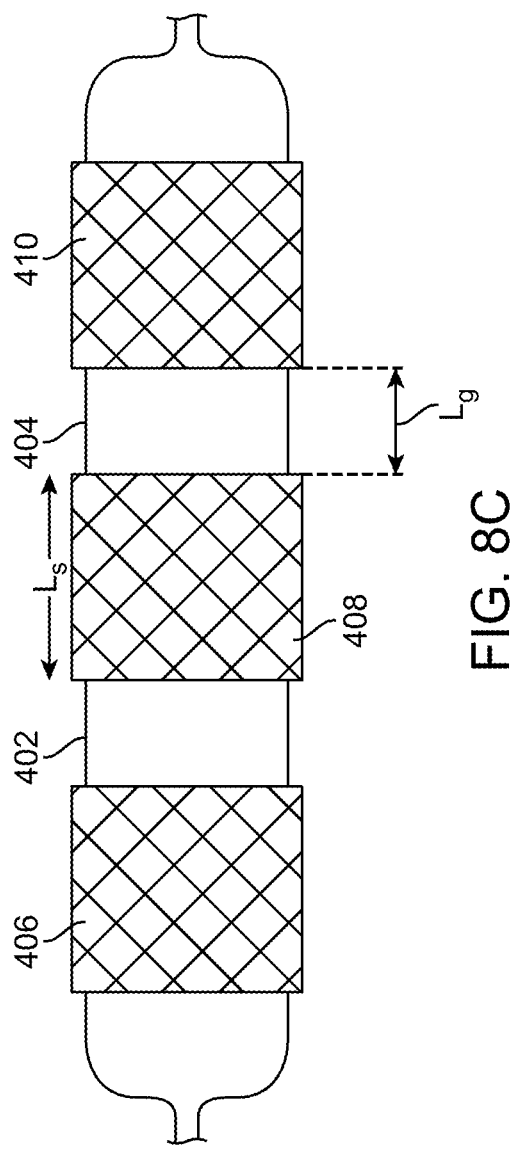
FIG. 8C depicts the balloon-scaffold assembly of FIGS. 8A-B when the balloon is in a completely inflated condition.

FIG. 8C depicts the balloon-scaffold assembly of FIGS. 8A-B when the balloon 400 is in a completely inflated condition. As shown in FIG. 8C, segments 406, 408, and 410 are in fully expanded states due to inflation of the balloon. The length Ls of each segment has decreased due the expansion. The width, Wr, of the pre-pillowed sections 402, 404 increased during the expansion, and thus is larger than Wr in the deflated configuration. During the expansion to the fully expanded state, the segment to segment gap distance Lg is maintained to be the increasing width Wr of the pre-pillowed sections. Thus, gap distance between segments 406/408 and 408/410 remains the same during expansion.

The pillowed sections of the balloon can be made by a pre-pillowing process which includes applying heat and pressure to a balloon while allowing bands of balloon material to expand to a greater degree (i.e., diameter) than the remainder of the balloon. Applying heat results in raising the temperature above ambient, 20 to 30 deg C., of the whole balloon, only the balloon material of the bands, or only a localized region around the bands. Applying heat to the band or band regions only limits any negative effects the heat may have on the balloon material mechanical properties. The remainder of the balloon can be restrained from expansion completely or allowed to partially expand to a lesser degree than the bands.

Delivery balloons are typically loaded onto a catheter in a deflated, folded configuration. The heat and pressure may be applied when the balloon is an unfolded state or folded state. Therefore, the pre-pillowing process can be performed as part of the balloon folding process or as a separate step after the balloon folding process.

The heat and pressure may be applied when the balloon is in a deflated state, partially inflated state, or completely inflated state. For a noncompliant balloon, compete inflation may correspond to expanding the balloon to a maximum size without elastic or plastic deformation of the balloon material. The heat and pressure may cause the balloon material in the bands to plastically deform, while the material in the remainder of the balloon plastically deforms not at all or to a lesser degree than the balloon material in the bands.

When the pre-pillowing process is performed as part of the balloon folding process, the balloon may be partially or completely inflated and heated while allowing bands of balloon material to expand to a greater degree (i.e., diameter) than the remainder of the balloon. The expansion of the bands may correspond to plastic deformation.

The pre-pillowing process can be performed on a folded balloon in a partially or completely deflated state and includes heating while allowing bands of balloon material to expand to a greater degree (i.e., diameter) than the remainder of the balloon. The expansion of the bands may also correspond to plastic deformation. After the balloon material is expanded, the temperature is reduced to ambient and any inflated portions of the balloon are deflated, in particular, the bands.

The pre-pillowing process may be incorporated into the initial balloon shaping process. In this case, as the balloon is blown into a mold that forms the outside diameter of the balloon, the pre-pillow shape is also formed in the same process.

A balloon may be pre-pillowed by using a mold having a cylindrical cavity defined by walls having a first inside diameter. The mold has cylindrical recesses for forming the bands of pre-pillowed balloon material with a second inside diameter larger than the first inside diameter. A balloon is inserted into the mold and heat and pressure are applied inside the balloon. The first inside diameter may be the same or slightly larger to allow a slip fit of the balloon in the mold. The heat and pressure cause the balloon material at the recesses to expand into the recess which may expand against the walls of the recesses. The applied pressure is removed and the balloon is cooled or allowed to cool and then removed from the mold.

Figure 9:
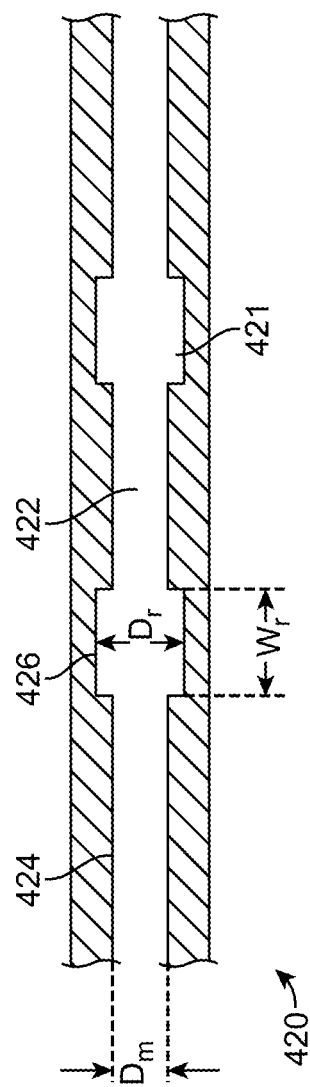
FIG. 9 depicts an axial cross-section of a cylindrical balloon pre-pillowing mold.

FIG. 9 depicts an axial cross-section of a cylindrical balloon pre-pillowing mold 420. Mold 420 has a cylindrical cavity 422 with axial sections with an inner diameter Dm and cylindrical recesses 421 with an inner diameter Dr and axial width Wr. The axial sections with inner diameter Dm are defined by walls 424 and the recesses by walls 426. A folded balloon with an outside diameter the same as or slightly less than Dm is disposed within cavity 422. The balloon is heated and the pressure is increased within the mold. The balloon sections located at recesses 421 expand within the recesses. These balloon sections may expand against walls 426 of recesses 421, creating raised bands of pre-pillowed balloon material with outer diameter Dr and width Wr.

The balloon pressure may be between ambient pressure to 40 psi, 40 to 80 psi, 80 to 120 psi, 120 psi to 180 psi, or greater than 180 psi. The temperature of the heated mold or the temperature of the balloon during heating may be 25 to 40 deg C., 40 to 60 deg C., 60 to 80 deg C., 80 to 100 deg C., or greater than 100 deg C. The balloon may be heated for 1 to 3 min, 1 to 5 min, 3 to 5 min, 5 to 8 min, or greater than 8 min. The balloon mold may be cooled actively with a cooled gas or allowed to cool at ambient temperature. The cooling time can be 1 to 3 min, 1 to 5 min, 3 to 5 min, 5 to 8 min, or greater than 8 min. Typical parameters for a pre-pillowing process are given in Table 1 below.

TABLE 1

Typical parameters for a balloon pre-pillowing process.

| | |
|---|---|
| Heating temperature | 80° C. |
| Air pressure to balloon | 175 psi |
| Heating time | 5 minutes |
| Cooling time | 5 minutes |

The scaffold segments may be crimped tightly on a delivery balloon using a crimping apparatus such as an iris crimper. The crimping process may include 2 stages, a pre-crimp process and a final crimp process. In the pre-crimp process, the diameter of the scaffold segments are reduced to an intermediate diameter prior to loading the scaffold segments on the balloon. The reason for the pre-crimp process is to reduce the size of the scaffold segments to allow greater accuracy of loading the segments on a balloon.

The scaffold segments in an as-fabricated condition are placed over a mandrel and arranged end to end. The scaffold segments are spaced apart axially at a distance such that when the segments are reduced to the pre-crimp diameter the segments do not make contact with each other. For example, the scaffold segments are placed over a stepped mandrel. The mandrel with the scaffold segments is loaded into the pre-crimper, for example, an iris crimper and crimped to the pre-crimp diameter. The pre-crimped scaffold segments may further be placed inside a protective sheath disposed in a outer surface of the each scaffold segment.

FIG. 10A depicts an assembly 430 including scaffold segments 438 positioned over a stepped mandrel 432. Stepped mandrel 432 has larger diameter sections 434 that step down to smaller diameter sections 436. Scaffold segments 438 are disposed over smaller diameter sections 436. The stepped mandrel with the loaded scaffold segments is placed into the jaws of the crimper. Once the crimper jaws have made contact with the scaffold segments the stepped mandrel is removed and replaced with a hooked mandrel (see FIG. 24B) After the crimping process the crimper jaws open up and the hooked mandrel is used to remove the scaffold segments from the crimper. Scaffold segments 438 have a reduced diameter and a longer axial length in the pre-crimped state.

The crimping of the segments from the initial diameter to the final diameter may be performed in two or more steps, where each step corresponds to crimping to an intermediate diameter between the initial and final crimped diameter. Each diameter reduction can include a dwell period before the next diameter reduction step. Additionally, the scaffold segments may be heated during the crimping process to increase the flexibility of the scaffold segments, which is expected to reduce fracturing in the scaffold during crimping.

Table 2 shows exemplary pre-crimper settings for crimping 0.30 in diameter scaffold segments to a final crimp diameter of 0.08 in. The crimper head temperature is about 48 deg C. and the inside diameter of the protective sheath is 0.125 in.

TABLE 2

Pre crimper settings

| Diameter (in) | Dwell (s) | Speed (in/s) |
|---|---|---|
| 0.3100 | 0 | 0.300 |
| 0.2650 | 30 | 0.005 |
| 0.2100 | 30 | 0.005 |
| 0.2200 | 1 | 0.005 |
| 0.1600 | 30 | 0.005 |

TABLE 2-continued

Pre crimper settings

| Diameter (in) | Dwell (s) | Speed (in/s) |
|---|---|---|
| 0.1300 | 30 | 0.005 |
| 0.0800 | 60 | 0.005 |

The pre-crimped segments are removed from the pre-crimper with a hooked mandrel. The segments are then placed into a protective sheath. The sheathed scaffolds may then be stored until the final crimping process.

The application of a therapeutic coating to the scaffold segments may be performed prior to the pre-crimping step. Alternatively, to limit coating damage, the coating step can be performed after the pre-crimp process.

The pre-crimped segments may then be loaded onto a pre-pillowed balloon catheter with pre-pillowed section, as described above. The segments are placed over the balloon between and next to the pillowed sections. The segments and balloon are then crimped down to about 0.0600 in with pressure applied at multiple steps with a dwell period between steps to achieve segment retention on the balloon. Pressure may be applied to the balloon during the final stages of the crimp process to enhance the scaffold retention to the balloon in the crimped state. When the catheter is removed from the crimper a protective sheath is placed over the scaffold segments.

Table 3 shows typical final crimper settings for crimping pre-crimped 0.125 in diameter scaffold segments to a final crimp diameter of 0.06 in. The crimper head temperature is 48 deg C. and the diameter of the inner protective sheath is 0.092 in. The crimping pressure used was 100 psi.

TABLE 3

Final crimper settings

| Diameter (in) | Dwell (sec) | Speed (in/sec) | Pressure Hold Time (sec) | Interrupt |
|---|---|---|---|---|
| 0.1100 | 20 | 0.050 | 5 | Yes |
| 0.1150 | 2 | 0.300 | 0 | No |
| 0.1100 | 30 | 0.005 | 30 | No |
| 0.1000 | 30 | 0.005 | 30 | No |
| 0.0650 | 60 | 0.001 | 50 | No |
| 0.0625 | 30 | 0.001 | 0 | no |
| 0.0610 | 30 | 0.001 | 0 | no |
| 0.0600 | 255 | 0.001 | 0 | no |

As discussed in the above embodiments, the segment to segment gap of a segmented scaffold changes as the segments are expanded to a deployed diameter. Deployment of a segmented scaffold with pre-pillowed segments provides for a consistent segment to segment gaps. However, even though the gaps between segments can be the same due to the pre-pillowed sections, the gaps still increases with deployed diameter. The increase in the segment to segment gap with deployment can become undesirably large.

Further embodiments of the present invention include methods and systems for deploying segmented scaffolds that have a predetermined gap at full deployment of the segmented scaffold. The predetermined gap may be smaller than that obtained by expansion of axial segments over a balloon of constant length.

Conventional delivery balloons are designed to stay the same length during inflation and expansion. This allows the scaffold to be deployed with minimal distortion to the scaffold. Certain embodiments of the present invention include deployment of a segmented scaffold with a delivery balloon that reduces the increase in the gap size between segments when the balloon is inflated and expands the scaffold.

In some embodiments, a segmented scaffold may be delivered by a balloon that shortens as it expands. A plurality of disconnected scaffold segments are crimped to a shortening balloon with the segments arranged end to end. Adjacent segments are spaced apart by a gap. The balloon is inflated which radially expands the axial segments and the balloon shortens as it inflates and expands. The balloon length in the fully expanded state can be 90 to 95%, 85 to 90%, 80 to 90%, or less than 80% of the diameter of the balloon in the deflated state. The shortening of the balloon can partially or completely counteract the shortening of the segments as they increase in diameter which reduces the growth of the gap. The rigidity of the segments can minimize distortion of the segments.

FIG. 11A depicts a balloon assembly 500 that includes a balloon 501 in a deflated state with a length Lb. Three scaffold segments 502, 504, and 506 are crimped over balloon 501 end to end with a gap 508, with a length Lg, between segments 502 and 504 and a gap 510 between segments 504 and 506. When balloon 501 inflates and expands 512, Lb decreases. FIG. 11B depicts balloon 501 in its fully expanded state and its length, Lb, has decreased. The segments have been expanded and their length, Ls, has decreased. However, the shortening of balloon 501 has counteracted the shortening of the segments, so Lg between the segments is the same in the expanded state.

A delivery balloon that shortens as it inflates can have a wall including or made of two or more layers of material. At least two of the layers can have different properties, such as modulus or durometer hardness. For example, the wall can be made of two or more layers of Pebax®, a polyether block amide made by Arkema, which causes the balloon to shorten when expanded.

The different layers may have different preferential polymer chain orientation. The layers of the balloon walls can be treated to induce preferential orientation in a specific direction to provide the elasticity and rigidity without being prematurely ruptured during deployment. For example, at least one layer may have polymer chains preferentially radially aligned so that the balloon can withstand high inflation pressures. Another layer could have polymer chains aligned preferentially in the longitudinal direction. Preferentially longitudinal orientation would reduce, inhibit, or minimize longitudinal stretch of the balloon perimeter as the balloon inflates. After the balloon unfolds and continues to expand, it will get shorter as the longitudinal perimeter increases in diameter.

In another embodiment, a balloon that shortens as it expands has a ring or band wrapped around the circumference of an axial section of the balloon between the scaffold segments crimped over the balloon. When the balloon is in a deflated condition, the inner diameter of the band may be the same or slightly larger than the outer diameter of deflated balloon so that the band is tightly fit over the balloon. The band may be fit tightly enough so that it does not move axially along the balloon. Alternatively, when the balloon is in a deflated condition, the inner diameter of the band may be less than the outer diameter of deflated balloon so that the band squeezes the balloon and reduces the diameter of the balloon at the location of the band. For example, the band can reduce the diameter by less than 5%, 5 to 10%, 10 to 20%, 20 to 30%, or more than 30%.

When the balloon is inflated, the band inhibits expansion of the balloon between the scaffold sections causing shortening of the balloon as it expands. A balloon that includes three or more segments can include bands in one or more of the gaps between the segments.

The band can be made of the any number of biocompatible materials. The band may be made of a rigid material that does not expand radially when the balloon inflates. For example, the band may be made of a bioabsorbable polymer such as PLLA or a PLLA-based polymer. Alternatively, band may be made of a metal such as stainless steel. Alternatively, the band can be made of a material that is flexible or elastomeric so that the material can expand radially when the balloon is inflated while still restricting expansion of the balloon as the location of the band. For example, flexible materials include polycaprolactone, polydioxanone, or a biocompatible crosslinked rubber.

As the balloon inflates, the rings restrict the balloon expansion at its axial location in the gaps between the segments. The balloon expands in the axial portions next to the bands which results in expansion of the segments. The localized restriction or reduction of expansion in the gaps causes the balloon to shorten as the diameter of the balloon increases in the adjacent axial sections that are not restricted. As a result, the increase in the segment spacing is reduced. The segment spacing can remain constant during inflation or be reduced during the inflation.

FIG. 12A depicts a delivery balloon 520 with rigid bands 522 and 524 disposed around balloon 520 at two axial positions. Scaffold segments can be crimped over balloon 520 between bands 522 and 524 and to the left of band 522 and to the right of band 524. FIG. 12B depicts balloon 520 in a partially inflated state and FIG. 12C depicts balloon 520 in a fully inflated state. As shown in both FIGS. 12B and 12C, bands 522 restrict the expansion of balloon 520 since there is a minimum in the diameter of the balloon at the bands. On either side of the bands, there is a tapered portion 526 of the balloon in which the balloon diameter increases from the minimum at the band and increases to a maximum expanded portion 524.

The band width should be wide enough so as not to cut into the balloon as it expands and is stressed locally at the bands. Band widths of 0.02 in to 0.20 in and more specifically about 0.06 in can be used. The best use of the band is as a spacer for separating and setting the crimped segment spacing so as to achieve the desired deployed spacing gap. This gap will be dependent on the amount the balloon shortens and the amount the segments shorten. Preliminary experiments to date indicate that a space between balloon segments can be shortened by ~1.5 mm when expanded to 6 mm diameter. Balloons can be from 20 mm long to 120 mm long or longer, depending on the number of segments to be delivered. The balloon diameters for delivery in the SFA are typically 5 to 7 mm, but the diameter may be from less than 3 mm, 3 mm to 10 mm, or greater than 10 mm. Balloon shortening is dependent on balloon material, balloon folded and expanded diameters, band width and diameter, number of bands and their spacing along the balloon length.

In an alternative embodiment, segments can be crimped over individual balloons arranged end to end over a catheter. In another alternative embodiment, a balloon can include individual balloon chambers with tapered portions between each chamber. The tapered portions shorten as the balloon is expanded.

In further embodiments, scaffold segments can be deployed in sequence such that the gap between adjacent deployed scaffolds is a selected gap size. In particular, such embodiments include selecting a gap size between implanted scaffold segments of a segmented scaffold. The first scaffold segment is positioned at an implant site and is at a reduced crimped diameter. The first segment is deployed at the implant site at an expanded diameter. A second scaffold segment is then positioned at an implant site proximal to the deployed first segment in a reduced crimped diameter. The second segment is deployed at an expanded diameter in such a way that the gap between the deployed first scaffold segment and deployed second scaffold is the selected gap size. A third, fourth, or any number of segments can be deployed by repeating the procedure described above. The space between each pair of scaffolds can be any desired or required any gap size.

In the embodiments of sequential deployment, two segments can be deployed at any required spacing. Radiopaque markers on the segments can make he segments visible in X-ray imaging, so a physician can use the imaging to position each segment relative to the previously deployed segment. The physician has maximum versatility in positioning the segments by deploying segments at different spacing and at different locations. For areas with high calcification, segments can be deployed within other segments.

A system for deploying scaffold segments sequentially can include a sheath with an inner lumen and distal end with an opening and one or more delivery balloons disposed within the lumen. The system can further include a first scaffold segment and a second scaffold segment arranged end to end crimped over the one or more balloons such that the balloons and scaffold segments are slidable or movable along the longitudinal axis within the lumen.

A method of delivering a segmented scaffold with such a system includes selecting a gap size between implanted scaffold segments of a segmented scaffold. The sheath including the balloon and scaffold segments is positioned distal to implant sites for scaffold segments. The first scaffold segment is distal to the second segment. The balloon and scaffold segments are slid distally through the inner lumen of the sheath to extend the first scaffold segment out of a distal opening of the sheath. The first scaffold segment is then deployed at a first implant site by inflating and expanding the balloon outside the distal opening of the sheath. After deployment of the first scaffold segment, the second scaffold segment is slid distally through the inner lumen to extend the second scaffold segment out of the distal opening to a second implant site proximal to the deployed first scaffold segment. The second scaffold segment is deployed at the second implant site. A gap between the deployed first scaffold segment and the deployed second scaffold segment is the selected gap size.

Figure 13A:
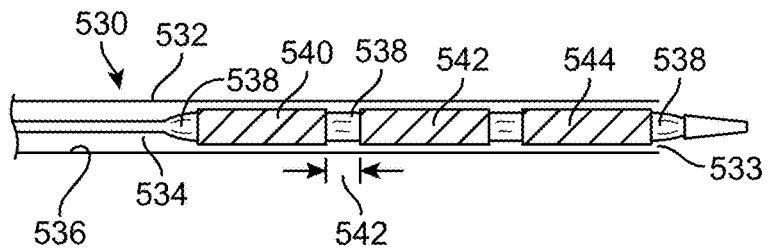
FIG. 13A depicts a system for deploying multiple scaffold segments that includes three scaffold segments over a balloon disposed within a sheath.

FIGS. 13A-E depict a system 530 and method for deploying multiple scaffold segments of a segmented scaffold sequentially at any required spacing between any of the segments. FIG. 13A shows that system 530 includes a sheath 532 with an inner lumen 534 and an inner surface 536. A balloon 538 is disposed within lumen 534. Scaffold segments 540, 542, and 544 are spaced apart and crimped over balloon 538 inside of lumen 536. The inner diameter of sheath 532 may be the same or slightly larger than the outer diameter of the crimped scaffold segments.

Figure 13B:
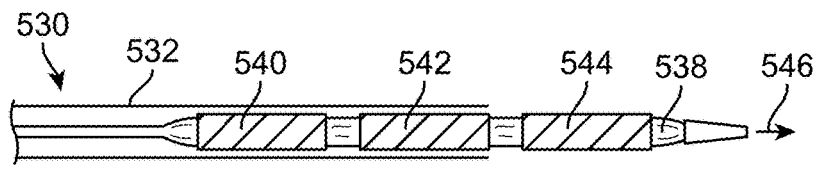
FIG. 13B depicts the system of FIG. 13A with the most distal segment extended out of sheath.

As shown in FIG. 13B, balloon 538 and the segments are slide distally through inner lumen 534 until the most distal segment, segment 544, is extended out of sheath 532 through distal opening 533 as shown by arrow 546. Alternatively, the system can be delivered to the deployment site with segment 544 already extended distally of the sheath 532.

Figure 13C:
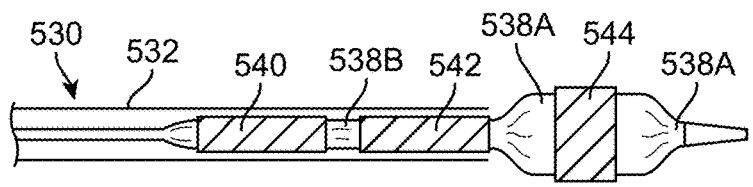
FIG. 13C depicts the system of FIGS. 13A-B with the balloon and segment outside the sheath fully expanded.

As shown in FIG. 13C, balloon 538 is inflated and the section 538A of balloon 538 outside of sheath 532 expands, which expands and deploys segment 544. Sheath 532 prevents expansion of the section 538B of balloon 538 under segments 540 and 542 from expanding. In alternative, embodiments, the diameter of sheath 532 is greater than the outer diameter of the segments and balloon 538 can expand partially inside of sheath 532, which partially expands segments 540 and 542. For example, the inside diameter of sheath 532 can be 110 to 120%, 110 to 150%, or 120 to 150% of the outer diameter of the segments inside the sheath, which allows expansion of the segments to the inner diameter of the sheath 532.

Figure 13D:
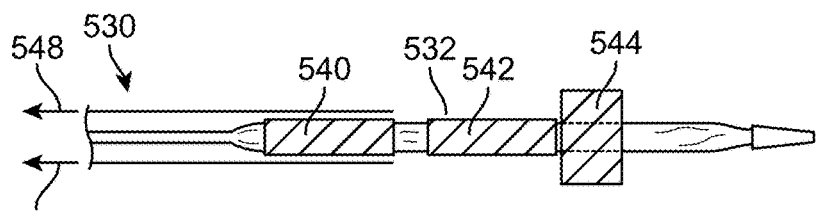
FIG. 13D depicts the system of FIGS. 13A-C with the second most distal segment extended out of the sheath.

FIG. 13D shows that after deployment of segment 544, balloon 538 is deflated and sheath 532 is retracted, as shown by arrows 548, from over segment 542. Segment 542 is advanced and positioned proximal to deployed segment 544.

Figure 13E:
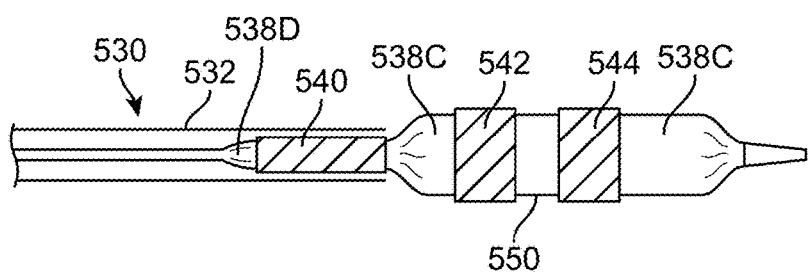
FIG. 13E depicts the system of FIGS. 13A-D with the second most distal segment fully expanded.

As shown in FIG. 13E, balloon 538 is then inflated and section 538C of balloon 538 outside of sheath 532 expands, which expands and deploys segment 542. Sheath 532 prevents expansion of the section 538D of balloon 538 under segment 540. Segment 542 is positioned prior to its deployment relative to segment 544 so the gap 550 between segments 542 and 544 after deployment is a desired or selected gap size. The process may be continued to deploy segment 540 and any number of additional segments with desired gap sizes between deployed segments.

Another embodiment of a system for deploying a segmented scaffold in sequence includes a sheath with a first scaffold segment and a second scaffold segment. In this embodiment, the first scaffold segment is distal to the second scaffold segment and only the first scaffold segment is crimped over the balloon. The first scaffold segment and balloon are axially slidable relative to the second scaffold segment.

When the first scaffold segment is positioned outside the sheath, the first scaffold segment is delivered by inflating and expanding the balloon at a first implant site. After deployment of the first scaffold segment, the balloon is deflated and then slid proximally into the inner lumen of the sheath within the second scaffold segment. The second scaffold segment is then secured over the balloon. The balloon can be secured through a slight inflation of the balloon while still inside of the sheath. The second scaffold segment secured over the balloon is then slid distally through the distal opening out of the sheath to a second implant site proximal to the deployed first scaffold segment and deployed at the second implant site by the balloon. A gap between the deployed first scaffold segment and the deployed second scaffold is the selected gap size. Additional segments inside the sheath can be delivered by repeating the process described.

Figure 14A:
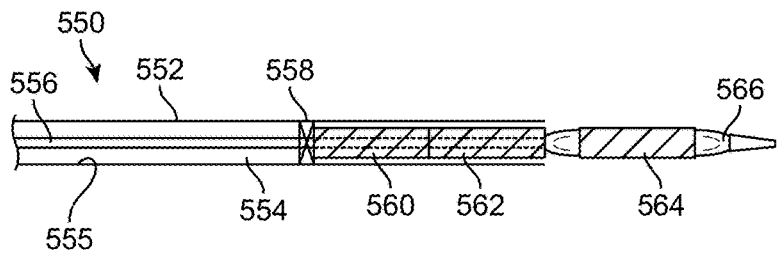
FIG. 14A depicts a system for deploying multiple scaffold segments of a segmented scaffold at any required spacing with two proximal segments in a sheath over a guide wire and a distal segment outside the sheath crimped over a balloon.

FIGS. 14A-H illustrate a system 550 and method for deploying multiple scaffold segments of a segmented scaffold sequentially at any required spacing. FIG. 14A shows that system 550 includes a sheath 552 with an inner lumen 554 with an inner surface 555. Scaffold segments 560 and 562 are positioned over inner sheath 556 within lumen 554 of sheath 552. A proximal end of scaffold segment 560 is positioned against a hard stop 558. The inner diameter of sheath 552 may be the same or slightly larger than the outer diameter of the scaffolds. Scaffold segment 564 is positioned distal to scaffold segment 562 outside of sheath 552. System 550 can be delivered to the implant site in the configuration shown or with scaffold segment 564 and balloon 566 within sheath 552. In this case, once sheath 552 is positioned proximal to an implant site, scaffold segment 564 is extended out of sheath 552 or sheath 552 is retracted so that scaffold segment is outside of sheath 552.

Figure 14B:
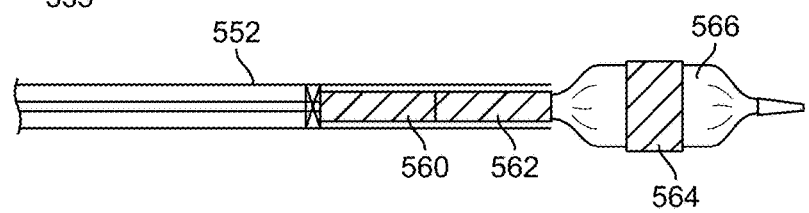
FIG. 14B depicts the system of FIG. 14A with the distal segment deployed by the inflated balloon.

As shown in FIG. 14B, scaffold segment 564 is deployed to a larger diameter by inflation and expansion of balloon 566. The recoil caused by self expanding properties of the segments inside of the sheath will help hold undeployed segments inside sheath 552.

Figure 14C:
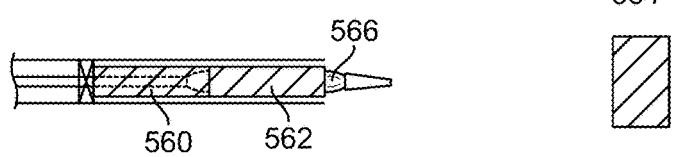
FIG. 14C depicts the system of FIGS. 14A-B with the balloon deflated and drawn within the second most distal segment within the sheath.

Referring to FIG. 14C, after deployment of scaffold segment 564, balloon 566 is deflated and drawn or slid back relative to scaffold segments 560 and 562. Balloon 566 is drawn within scaffold segment 562 and sheath 552 is retracted. Scaffold segment 562 is secured onto balloon 566 which can be performed by inflating balloon 566 slightly while scaffold 562 is still within sheath 552.

Figure 14D:
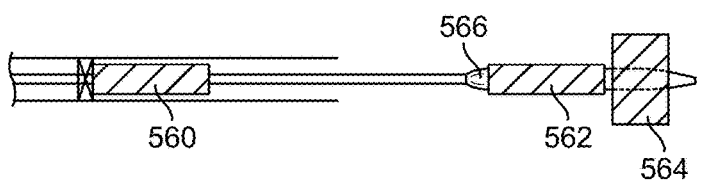
FIG. 14D depicts the system of FIGS. 14A-C with the second most distal segment advanced out of the sheath.
Figure 14E:
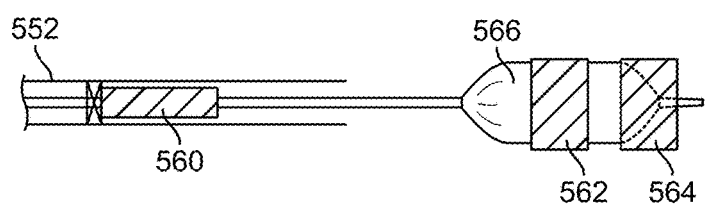
FIG. 14E depicts the system of FIGS. 14A-D with the second most distal segment deployed.

Referring to FIG. 14D, balloon 566 is advanced out of sheath 552 toward deployed segment 564 and positioned adjacent to it. FIG. 14E shows balloon 566 inflated and expanded, which deploys segment 562 at a selected spacing from segment 564.

Figure 14F:
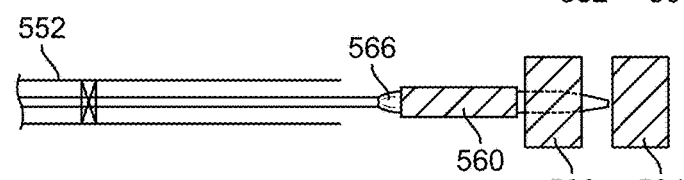
FIGS. 14F-H depict the system of FIGS. 14A-E with the steps illustrated in FIGS. 14C-E repeated to deploy the final desired number of segments.
Figure 14G:
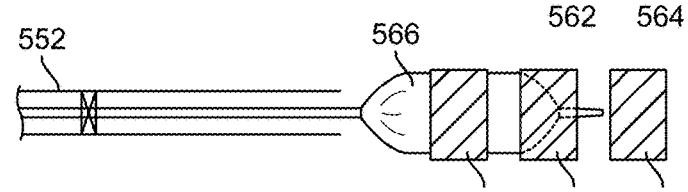
Figure 14H:
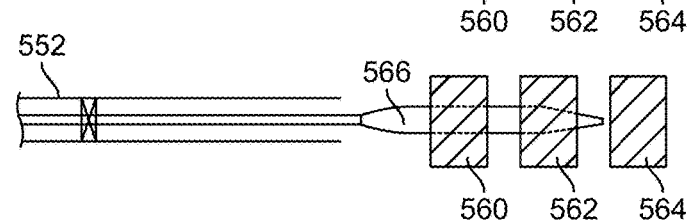

The process of FIGS. 14C-E is repeated to deploy the final segment 560 at a desired spacing from segment 562, as shown in FIGS. 14F-H. The process can continued until any desired number of segments has been sequentially deployed at the desired spacings. When all the segments have been deployed the balloon and sheath can be retracted and removed from the patient.

The embodiments in FIGS. 13A-E and 14A-H provide a physician with maximum versatility in deploying segments at different spacing and at different locations. In some embodiments, segments can be deployed within a previously deployed segment. This may be useful in vessel areas with high calcification. For example, in FIGS. 14D-F, segment 562 can be advanced within segment 564 and deployed within segment 564.

Figure 15A:
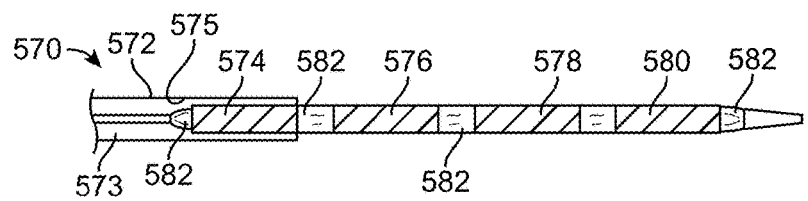
FIGS. 15A-B depict a system for deploying multiple scaffold segments of a segmented scaffold.
Figure 15B:
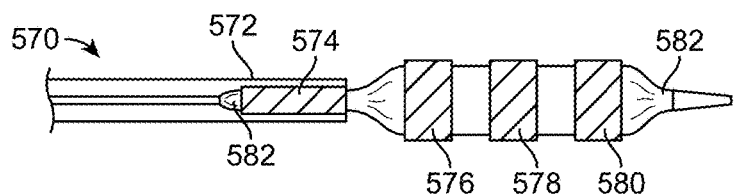

In further embodiments, two or more segments can be deployed simultaneously in a vessel by one long balloon and one or more additional segments can be deployed sequentially after their deployment. The one or more additional segments can be deployed by the same balloon or by a different balloon. FIG. 15A depicts a system 570 and method for deploying multiple scaffold segments of a segmented scaffold. In FIG. 15A, system 570 includes a sheath 572 with an inner lumen 573 and an inner surface 575. Scaffold segments 576, 578, and 580 are arranged end to end and positioned outside or distal of sheath 572. Segments 576, 578, and 580 are crimped over balloon 582 which is in a deflated condition. Balloon 582 extends proximally into sheath 572. Scaffold segment 574 is positioned over balloon 582 within sheath 572. As shown in FIG. 15B, balloon 582 inflates and expands outside of sheath 572 which deploys segments 576, 578, and 580 within a vessel. Sheath 572 prevents inflation of balloon 582 within sheath 572. After deployment, balloon 582 is deflated and segment 574 is advanced out of sheath 572. Segment 574 can then be deployed with balloon 582 with a selected spacing from segment 576. This spacing may be from 1-2 mm, 2-5 mm or even in a different location within the vessel.

In some embodiments, a constant segment to segment spacing is maintained during and after simultaneous deployment of only two scaffold segments. A band of raised balloon material in the gap, as disclosed herein, maintains the constant width of the gap between the segments.

Figure 16A:
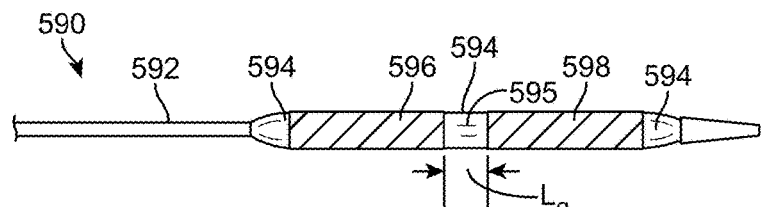
FIGS. 16A-D depict a system for and method of deployment of two scaffold segments with a constant spacing during deployment.

FIG. 16A depicts a system 590 including a deflated balloon 594 that is positioned within a vessel lumen by a guide wire 592. Scaffold segments 596 and 598 are crimped over balloon 594. Segments 596 and 598 are spaced apart by a gap. A band 595 of raised or pre-pillowed balloon material is in the gap. The gap width, Lg, is the same as the width of band 595.

Figure 16B:
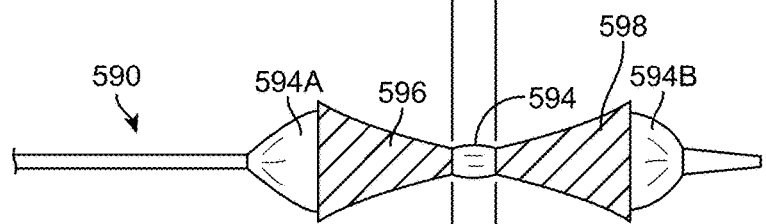
Figure 16C:
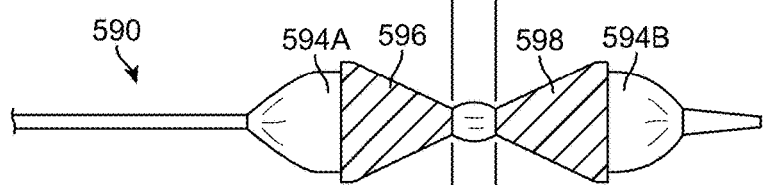
Figure 16D:
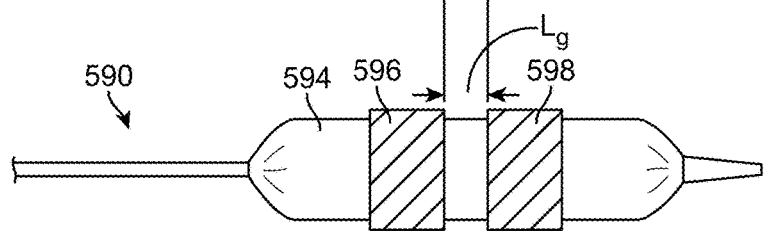

As shown in FIGS. 16B-C, as the balloon inflates, it takes on a dog bone shape in which ends 594A and 594B of balloon 594 inflate first and also expand the corresponding ends of segments 596 and 598 first. Segments 596 and 598 shorten as they expand, however, they are pushed against the band of pre-pillowed balloon material. As the balloon expansion continues, the segments shorten and slide on the balloon to maintain a constant center spacing. FIG. 16D depicts balloon 594 completely inflated with segments 596 and 598 fully expanded and deployed. The gap width, Lg, has remained constant during inflation and deployment of the segments.

In further embodiments, the gap between deployed segments can be adjusted after partial deployment by shortening the balloon. In such embodiments, after partial deployment of scaffold segments through expansion of a balloon, a proximally directed force is applied to the balloon to shorten the balloon to reduce the width of the gap between the segments to a desired gap width. The partially inflated balloon can include a pinched or necked down region between the segments that has a reduced diameter. The force causes the balloon to fold into itself at the pinched region to allow the balloon to shorten and reduce the width of the gap.

A system for performing such a method can include an outer tubular member and an inner elongate member disposed within the outer tubular member. A delivery balloon is disposed over at least the inner elongate member. A proximal end of the balloon is attached to the outer tubular member and a distal end of the balloon is attached to a distal end of the inner elongate member. The inner elongate member is axially slideable within the outer tubular member. When the balloon is completely or at least partially inflated, sliding the inner tubular member proximally causes the balloon to shorten.

Figure 17A:
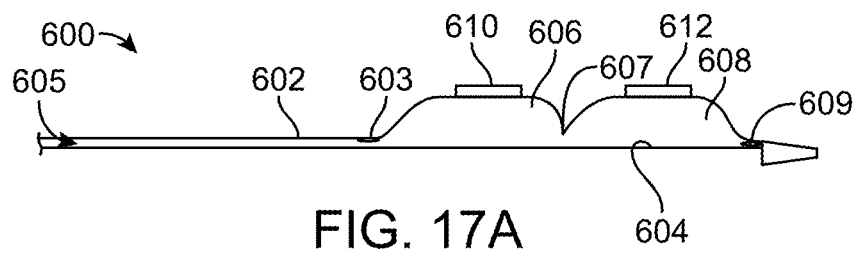
FIG. 17A depicts a half axial cross-sectional view of a delivery system for scaffold segments of a segmented scaffold with a pinched balloon in an inflated state.

FIG. 17A depicts a half axial cross-sectional view of a delivery system 600 including a pinched balloon in an inflated state with a proximal balloon section 606 and a distal balloon section 608. Expanded scaffold segments 610 and 612 are over balloon sections 606 and 608, respectively. The balloon has a pinched or necked down region 607 with a reduced diameter separating proximal balloon section 606 and distal balloon section 608.

Delivery system 600 further includes an outer member 602 disposed over an inner member 604. An inflation pressure applied into inflation lumen 605 between inner member 604 and outer member 602 inflates the balloon. A distal end 603 of proximal balloon section 606 is attached to outer member 602. A distal end 609 of distal balloon section 608 is attached to inner lumen 604. Inner member 604 is proximally slideable with respect to outer lumen 602, Referring to FIG. 17B, inner lumen 604 is slid or moved proximally with respect to outer member 602, as shown by an arrow 614. The balloon also slides or moves proximally due to a proximal force applied to distal balloon section 608 by inner member 604 as it slides. The proximal sliding of the balloon shortens the balloon and causes proximal and distal balloon sections to fold into each other which create folds 614, which shortens the gap between segments 610 and 612.

Figure 17B:
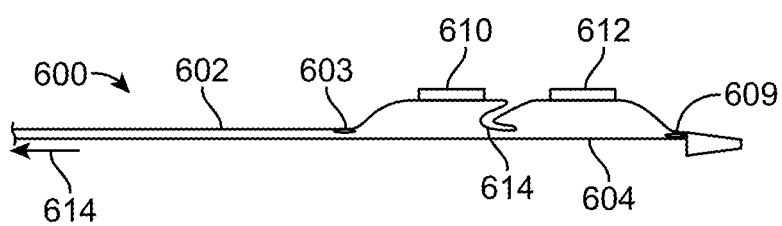
FIG. 17B depicts the system of FIG. 17A with the balloon shortened.
Figure 18A:
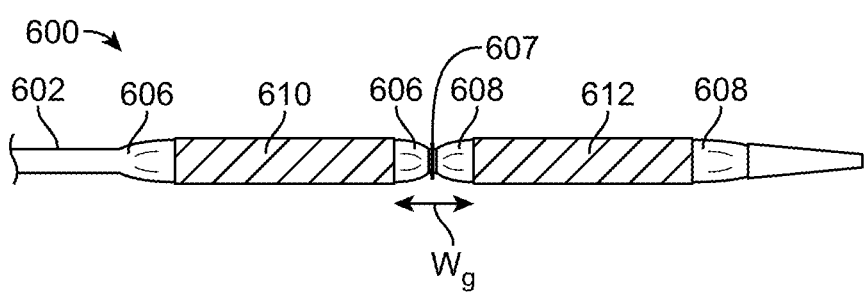
FIG. 18A depicts a side view of the system of FIG. 17A with the balloon in a deflated state.
Figure 18B:
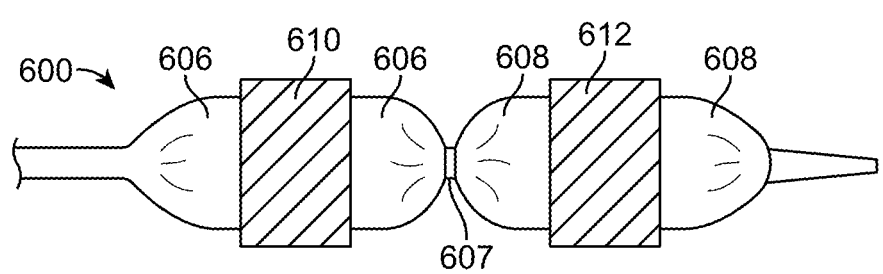
FIG. 18B depicts a side view of the system FIGS. 17A-B with the balloon in an inflated state and the segments expanded.
Figure 18C:
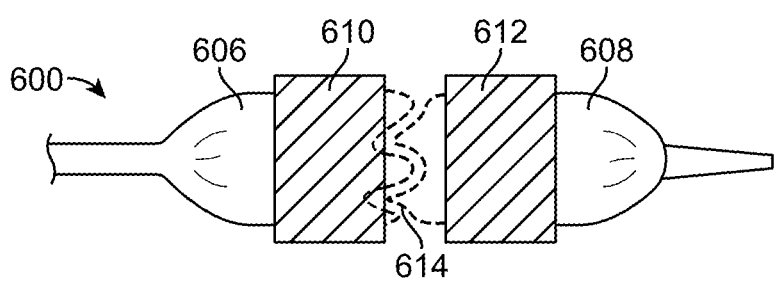
FIG. 18C depicts another side view of the system of FIG. 17B.

FIGS. 18A-C depict a side view of system 600 of FIGS. 17A-B. FIG. 18A shows system 600 with the balloon in a deflated state. Pinched or necked down region 607 has a reduced diameter compared to proximal balloon section 606 and distal balloon section 608. As shown in FIG. 18B, the gap width or spacing, Wg, increases between segments 610 and 612 after inflation or partial inflation and expansion or partial expansion of the balloon. FIG. 18C depicts system 600 after shortening the balloon by proximally sliding inner member 604. The sliding decreases the gap or spacing between segments 610 and 612 and creates folds 614.

In further embodiments, the spacing between scaffold segments during expansion can be maintained at a desired constant gap size or width with a spacer member. In such embodiments, a spacer member is attached to a balloon in a deflated state in a gap between segments. The spacer member is associated with each segment. When the balloon inflates and expands the scaffold segments, the spacer member maintains a constant gap size between the segments.

Figure 19A:
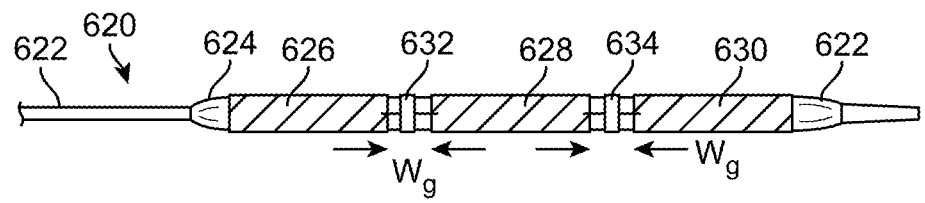
FIG. 19A-D depicts a system for and method for deploying scaffold segments of a segmented scaffold using spacer clips in gaps between scaffold segments.

FIG. 19A depicts a system 620 including a deflated balloon 624 that is positioned within a vessel lumen by a balloon catheter 622. Scaffold segments 626, 628, and 630 are crimped over balloon 624. Segments 626 and 628 and segments 628 and 630 are spaced apart by gaps, with a width Wg. Spacer clips 632 positioned in the gap between 626 and 628 and spacer clips 634 are positioned in the gap between 628 and 630. Spacer clips 632 and 634 are distributed around the circumference of balloon 624 in the respective gaps.

Spacer clips may be made of a metal or a polymer. For example, the spacer clips can be made of a biodegradable polymer, which may be the same as scaffold segment polymer. They may also be made of polycarbonate, stainless steel, or nitinol.

Spacer clips 632 and 634 are attached to balloon 624 and are also associated with segments on either side of the spacer clips. Spacer clips 632 and 634 are described in detail in FIGS. 20A-C.

Figure 19B:
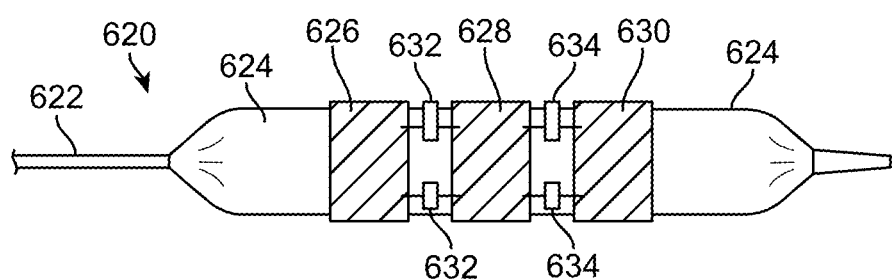

Balloon 624 inflates and expands segments 626, 628, and 630. FIG. 19B depicts system 620 after balloon 624 is inflated and the segments are expanded. During expansion of the segments, spacer clips 632 maintain the gap width at Wg between segments 626 and 628 and spacer clips 634 maintain the gap width at Wg between segments 628 and 630 due to the association of the clips with adjacent segments. Spacer clips 634 can maintain the gap between segments 628 and 630 at width different from that of segments 626 and 628. The segment lengths decrease during expansion, however, the spacer clips maintain a constant gap width between segments. If the distal set of clips are attached to the balloon and the other sets of clips are free to float on the balloon, as the balloon expands and the segments shorten, the segments will slide along the balloon towards the balloon attached set of clips, thus maintaining the segment to segment spacing.

Figure 19C:
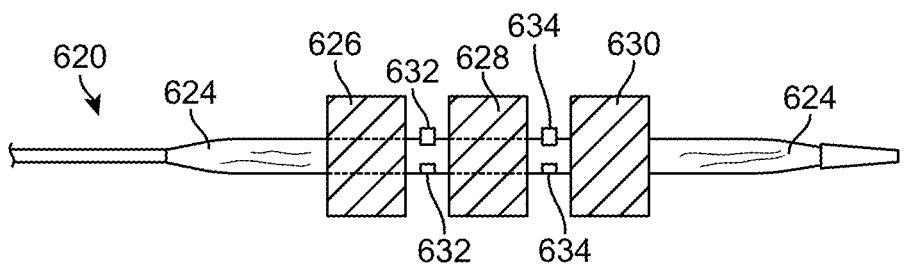
Figure 19D:
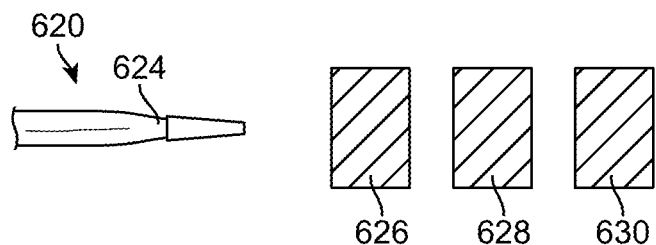

As shown in FIG. 19C, after deployment of the segments, balloon 624 is deflated. The deflation causes the diameter of the balloon to decrease. As balloon 624 deflates spacer clips 632 and 634 disassociate or are pulled away from the segments and remain attached to the balloon. FIG. 19D shows balloon 624 is retracted from the deployed segments after deflation.

Figure 20A:
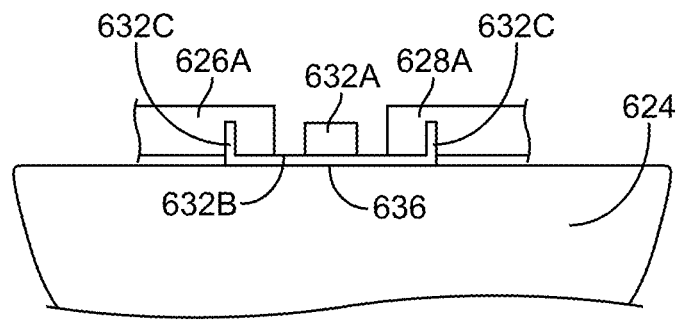
FIG. 20A depicts a close-up axial cross-sectional view of the gap region between segments of the system of FIGS. 19A-D.
Figure 20B:
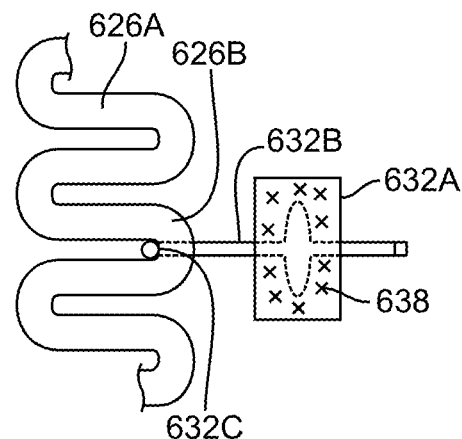
FIG. 20B depicts a close-up overhead view of the gap region between segments of the system of FIGS. 19A-D.

FIG. 20A depicts a close-up axial cross-sectional view and FIG. 20B depicts an overhead view of the gap region between segments 626 and 628 which shows an exemplary structure spacer clip 632 and association with adjacent segments. Spacer clip 632 has a portion 632A in the gap between struts 626A of segment 626 and struts 628A of segment 628. Portion 632A is attached to surface 636 of balloon 624. Portion 632A may be attached to balloon surface 636, for example, by laser bonding 638 or alternatively with an adhesive.

Spacer clip 632 has arms 632B which extend along the gap to struts 626A and 628B. Arms 632B have a bent or hooked portion 632C which engage the side walls of a crest of the struts of the segments on the side opposite to the gap, for example, crest 626B, as shown in FIG. 20B.

Figure 20C:
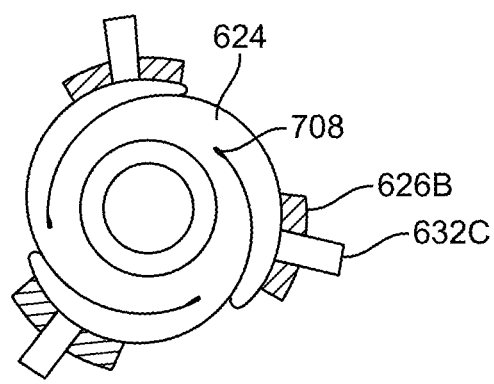
FIG. 20C depicts a radial cross-sectional view of the gap region between segments of the system of FIGS. 19A-D.

FIG. 20C depicts a radial cross-section of system 620 at crest 626B of segment 626. Balloon 624 is in a crimped folded configuration with folds 708 shown.

As balloon 622 inflates and expands the segments, the spacer clips apply forces on each segment which prevents movement of the segments away from each other due to shortening of the segments to maintain the gap width.

In some embodiments, segmented scaffolds may be coated with an antiproliferative drug. The spaces between the segments, in particular where there are balloon pillows, represent regions where there may be no drug. If the pillowed regions were large, then there may be a potential for focal stenosis developing where the balloon pillows touched the vessel wall. Coating the balloon with an antiproliferative drug will deliver the drug to the segment of the vessel wall. The drug can include paclitaxel, protaxel, taxotere, docetaxel, ortataxel, everolimus, sirolimus, myolimus, novolimus, temsirolimus, merilimus, deforolimus, or zotarolimus. In some embodiments, the drug coating can be applied to the entire balloon surface. Alternatively, the coating can be limited to the gap regions between the segments. The coating can be applied using known techniques such as direct fluid application, spraying, brushing, or dipping. The coating can be applied prior to forming pre-pillows. Alternatively, the coating can be formed after formation of the pre-pillows to avoid potential damage to the balloon coating during the pre-pillow formation.

The coating can also be applied after mounting the scaffold segments on the balloon. In this case, a coating can be applied to the scaffold segments as well. Alternatively, the coating can be selectively applied only to the gap regions of the balloon surface, for example, by shielding the scaffold segments during application. In another embodiment, the coating is applied to the entire working length of the balloon after formation of the pre-pillows, but before the scaffold segments are crimped on. The coating and drug applied to the gap regions of the balloon surface may be different than the coating and drug applied to the scaffold segments. The balloon coating can be applied before the pre-crimping, between pre-crimping and final crimping, or after final crimping.

The vessel regions between the segments can act as "hinge points" when the vessel bends and compresses, as there is no scaffold there. Hinge points may be more likely to develop focal restenosis due to the exaggerated flexing and potential injury at the hinge point. Coating the balloon pillows with a drug coating may prevent restenosis at these hinge points.

The coating on the balloon can be pure drug or a drug mixed with a polymeric carrier. The polymeric carrier can be bioresorbable polymer. Additional components may be present in the balloon coating including radiopaque contrast agents, iopromide, iohexol, surfactants, Tween 80, Tween 60, Tween 40, emulsifiers, poly(vinyl pyrrolidonone), glycerol, propylene glycol, shellac, and urea. Tween 40, 60, 80 can be obtained from Sigma-Aldrich. Tween 40 is polyoxyethylenesorbitan monopalmitate, Tween 60 is polyoxyethylene sorbitan monostearate, and Tween 80 is polyethylene glycol sorbitan monooleate.

When the segments are deployed, the drug on the balloon in the gaps makes contact with the vessel wall. At least some of the drug transfers to or adheres to the vessel wall and remains even after deflation and removal of the balloon from the treatment site.

The scaffold segments of the present invention can be made from variety of biodegradable polymers including, but not limited to, poly(L-lactide) (PLLA), polymandelide (PM), poly(DL-lactide) (PDLLA), polyglycolide (PGA), polycaprolactone (PCL), poly(trimethylene carbonate) (PTMC), polydioxanone (PDO), poly(4-hydroxy butyrate) (PHB), and poly(butylene succinate) (PBS). The scaffold segments can also be made from random and block copolymers of the above polymers, in particular, poly(L-lactide-co-glycolide) (PLGA) and poly(L-Lactide-co-caprolactone) PLGA-PCL. The scaffold can also be made of a physical blending of the above polymers. The scaffold segments can be made from PLGA including any molar ratio of L-lactide (LLA) to glycolide (GA). In particular, the stent can be made from PLGA with a molar ratio of (LA:GA) including 85:15 (or a range of 82:18 to 88:12), 95:5 (or a range of 93:7 to 97:3), or commercially available PLGA products identified as having these molar ratios. High strength, semicrystalline polymers with a Tg above body temperature include PLLA, PGA, and PLGA.

"Radial strength" is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely as only minimal additional force is required to cause major deformation. "Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e radial strength.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to plastic deformation and then fracture. The ultimate strength is calculated from the maximum load applied during the test divided by the original cross-sectional area.

"Modulus" may be defined as the ratio of a component of stress or force per unit area applied to a material divided by the strain along an axis of applied force that result from the applied force. For example, a material has both a tensile and a compressive modulus.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

EXAMPLES

Example 1: Pillowed Balloon to Set Segment Spacing

Figure 21A:
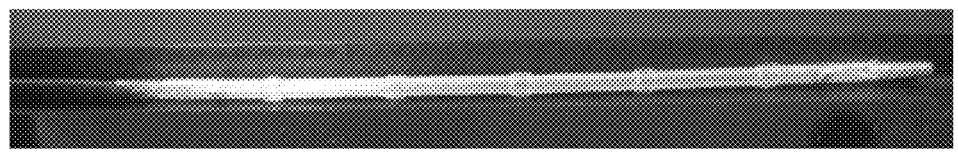
FIG. 21A depicts a photograph of a delivery balloon in a deflated state with pre-pillowed bands or sections to set scaffold segment spacing on the balloon.

FIG. 21A depicts a photograph of a delivery balloon in a deflated state with pre-pillowed bands or sections to set scaffold segment spacing.

Figure 21B:
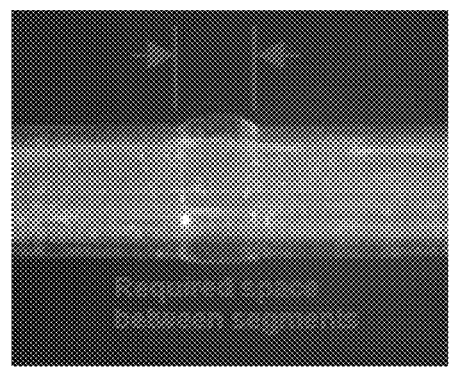
FIG. 21B depicts a close-up view of a pre-pillowed section of FIG. E1A.

FIG. 21B depicts a close-up view of a pre-pillowed section. With the pre-pillowing of the balloon, the segments not only maintain a consistent spacing during crimping, but also when deployed.

Figure 22:
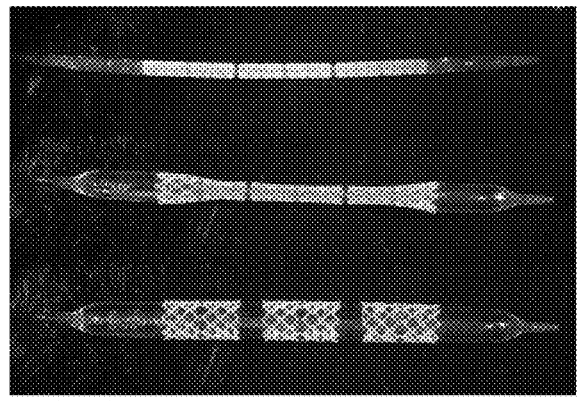
FIG. 22 illustrates the inflation process of a segmented scaffold.

FIG. 22 illustrates the inflation process of a segmented scaffold that shows that even segment spacing is maintained throughout expansion of the segments. The top picture shows a segmented scaffold crimped over a deflated balloon. The middle picture depicts the expansion when the balloon is partially inflated with the balloon having a dog bone shape. The ends of the balloon are inflated which partially expands the segments at the ends. The center of the balloon is partially or not inflated. The bottom picture shows the completely inflated balloon and the segments completely expanded. The balloon pre-pillowing maintains an even segment to segment spacing. The pictures show that the segment spacing increases during deployment, however, all spaces are the same.

Example 2: Animal Studies of Inflation of Balloon with Pre-Pillowed Sections

An animal study of the pre-pillowed balloon inflation with a segmented scaffold was performed using a porcine model. A balloon with pre-pillowed sections with a segmented scaffold first inflated at the ends creating a dog bone shape and then in the center of the balloon. The balloon shape change was observed by the contrasts shape under fluoroscopy. The final inflated balloon image showed even spacing of the implanted scaffold segments.

Figure 23A:
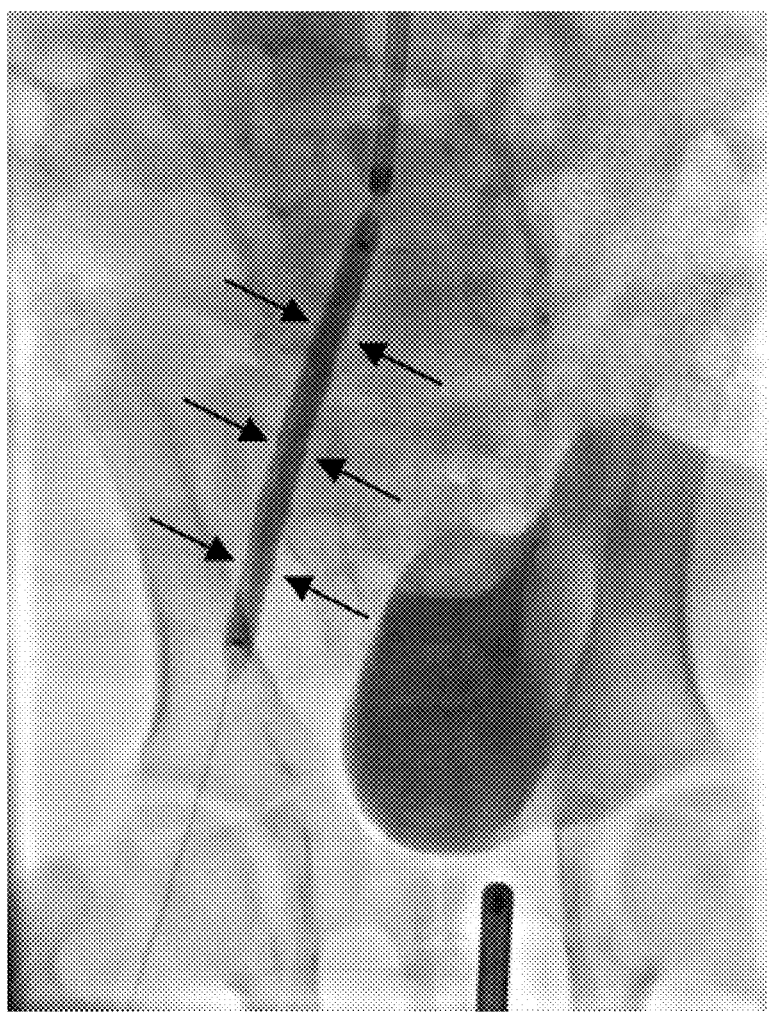
FIG. 23A depicts an implanted segmented scaffold in the Right External Iliac in the porcine model.
Figure 23B:
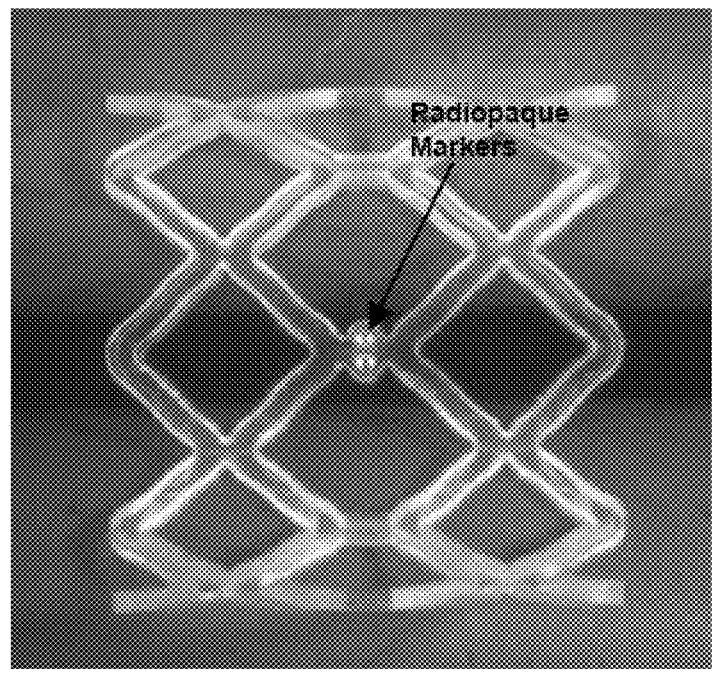
FIG. 23B depicts a close-up view of a segment which shows radiopaque markers in the scaffold segment.

FIG. 23A is a fluoroscopic image depicting implanted scaffold segments. FIG. 23A depicts the segmented scaffold implanted in the Right External Iliac in a porcine model. The even spacing of the radiopaque markers is shown by the arrows. The polymer scaffold does not show up under fluoroscopy so equal distance between markers signifies equal segment spacing. FIG. 23B is a close-up view of a segment which shows the radiopaque markers.

Example 3: Pre-Crimping and Final Crimping of Scaffold Segments on a Pre-Pillowed Balloon FIG. 24A depicts scaffold segments placed on a stepped mandrel for loading into a pre-crimper.

Figure 24A:
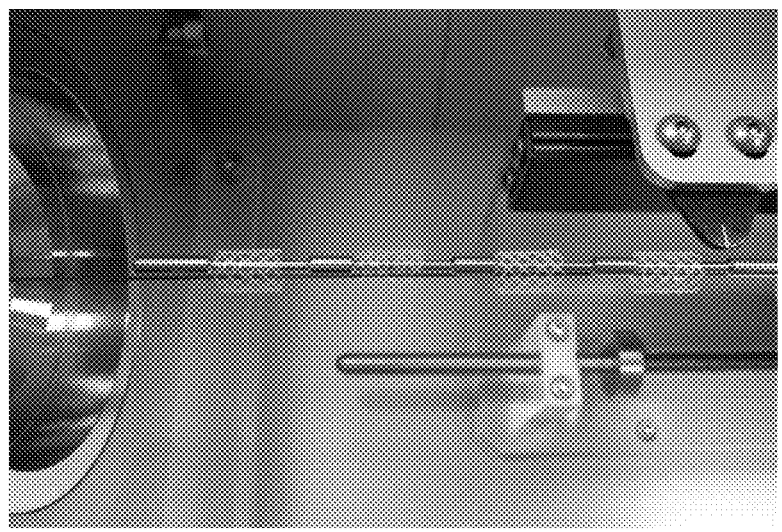
FIG. 24A depicts scaffold segments placed on a stepped mandrel for loading into a crimper to perform a pre-crimping process.
Figure 24B:
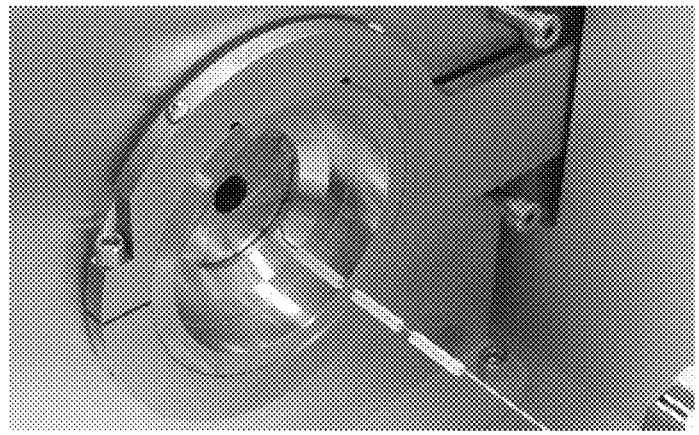
FIG. 24B depicts pre-crimped segments of FIG. 24A upon removal from the pre-crimper.

FIG. 24B depicts pre-crimped segments of FIG. 24A upon removal from the pre-crimper.

Figure 25A:
FIG. 25A shows pre-crimped segments of FIG. 24B loaded onto a pre-pillowed balloon.

FIG. 25A shows pre-crimped segments of FIG. 24B loaded onto a pre-pillowed balloon.

Figure 25B:
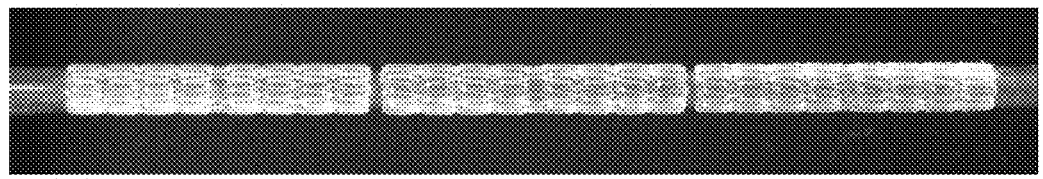
FIG. 25B shows the finished crimped segments of FIG. 25A.

FIG. 25B shows the finished crimped segments of FIG. 25A.

Figure 25C:
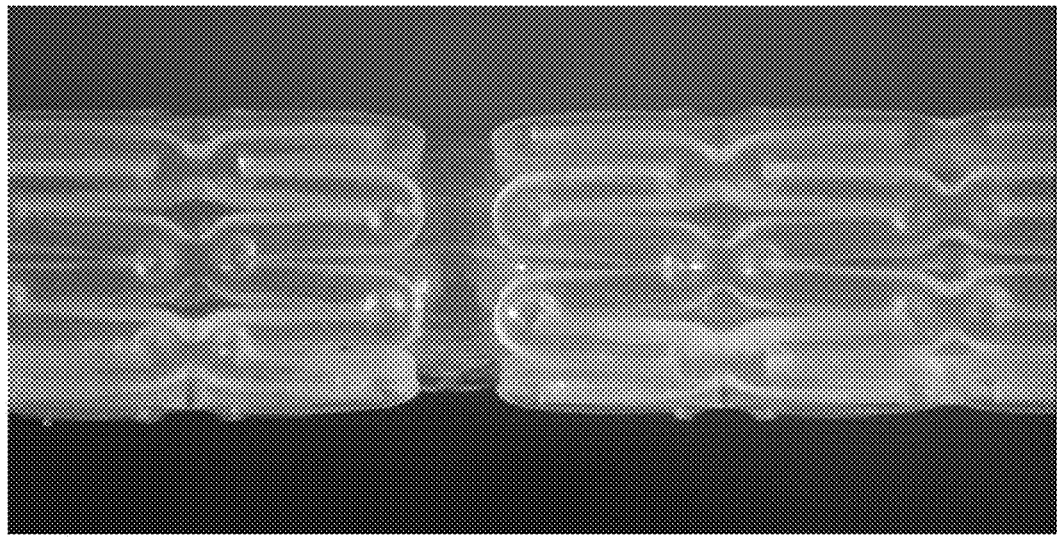
FIG. 25C is a close up view of the final crimped scaffold of FIG. 25B showing pillowing between the segments.

FIG. 25C is a close up view of the final crimped scaffold of FIG. 25B showing pillowing between the segments.

Example 4: Mechanical Test Results of Two Segmented Scaffold Designs

Figures 26A, 26B:
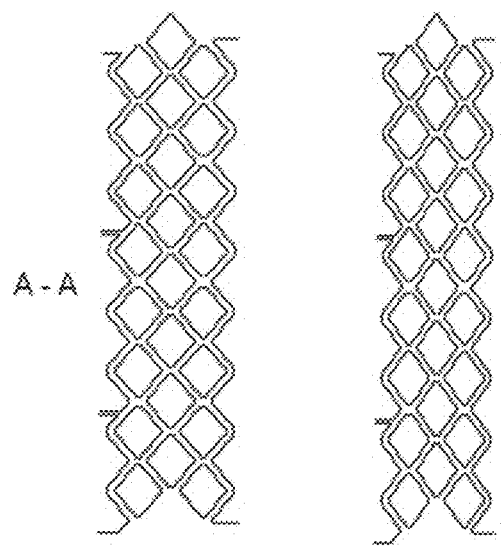
FIG. 26A-B depicts flattened views of two segmented scaffold designs.

Mechanical tests were performed on two segmented scaffold designs. FIGS. 26A-B depict flattened views of the two segmented scaffold designs. FIG. 26A depicts a "square-diamond" design ("S1") and FIG. 26B depicts a "tall diamond" design ("S2"). Line. A-A represents the cylindrical axis of the segments. FIG. 26A ("S1") has a diamond structure that is closer to a square than the one shown in FIG. 26B ("S2"). The S2 segment has a larger diamond cell height, Hc, than the square diamond segment. It is believed that the S2 segment will undergo more plastic deformation during crimping and then during expansion than the S1 segment.

The scaffold segments are laser cut from 7 mm expanded PLLA tubes. The segments have a 0.014 in strut width, 0.011 in strut radial thickness, and a 0.093 in crimped diameter. The properties of the scaffolds are given in Table 4.

TABLE 4

Properties of segmented scaffolds tested.

| Scaffold Design | Diamond Shape | Segment Length (mm) | Crimped Segment Space (mm) | Space at 5.3 mm OD (mm) | No. of Segments | Total Crimped Scaffold Length (mm) |
| --- | --- | --- | --- | --- | --- | --- |
| S1 | Square | 15.8 | 1.5 | 4.8 | 3 | 50 |
| S2 | Tall | 14.7 | 0.5 | 5 | 3 | 45 |

The following functional characteristics of the two scaffolds were measured and compared with two scaffold designs that are non-segmented, NS1 and NS2. The non-segmented designs are similar to the design in FIG. 1, which are composed of a plurality of zig-zag rings connected by links. The non-segmented scaffolds are made from PLLA tubes. The following properties were measured: dislodgement force, post dilate to fracture, diameter recoil, radial strength and stiffness, and crush recovery.

Figure 27:
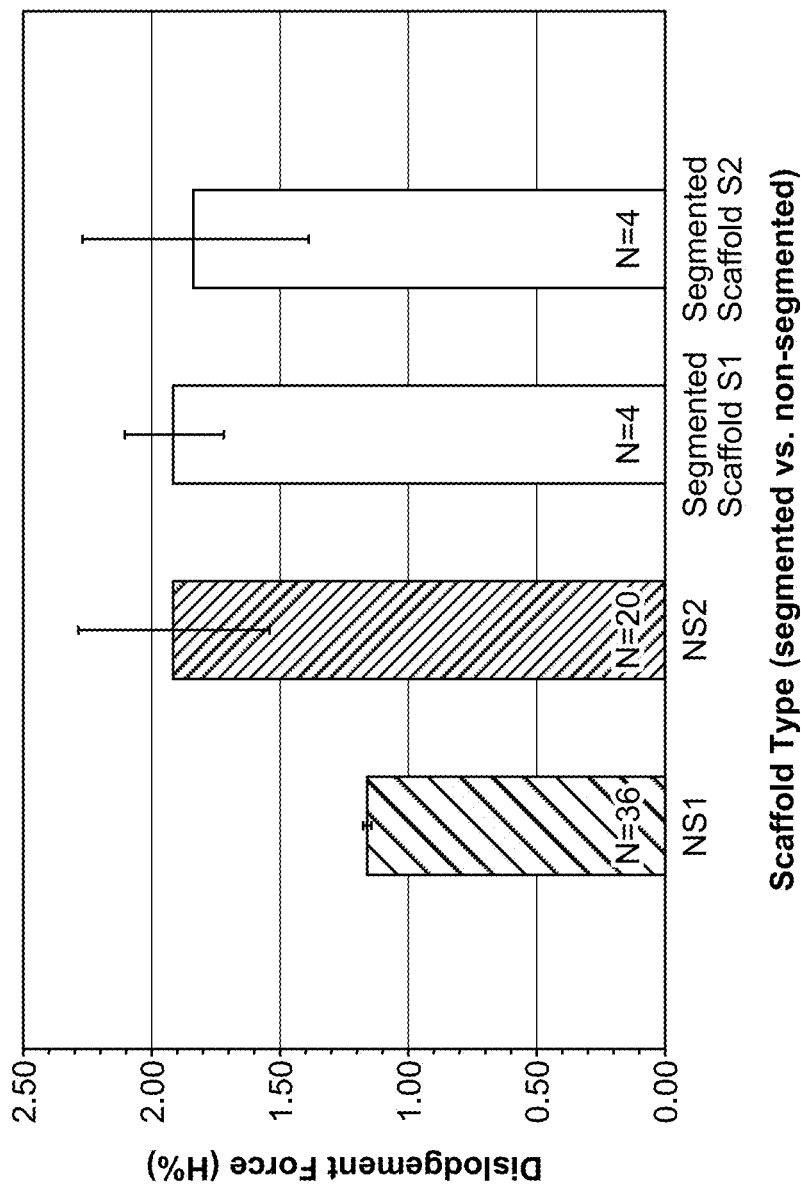
FIG. 27 depicts the dislodgment force in $lb_f$ for segmented and non-segmented scaffold designs.

FIG. 27 depicts the dislodgment force in $lb_f$ for the four scaffold designs. The dislodgement force is the axial force required to axially dislodge a crimped scaffold or segment off a balloon. The dislodgement forces for S1 and S2 are for the distal segment only.

Figure 28:
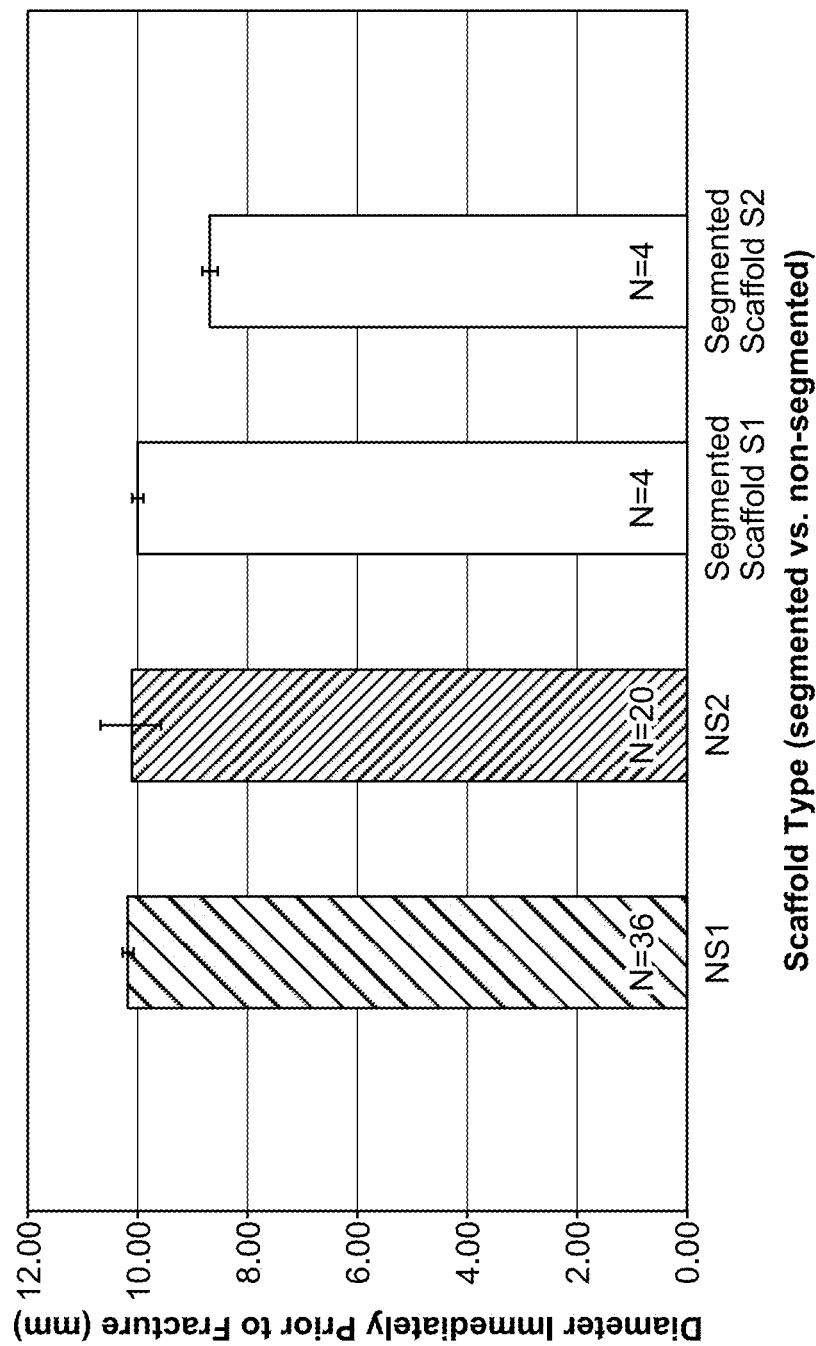
FIG. 28 depicts the post dilate to fracture in mm diameter for segmented and non-segmented scaffold designs.

FIG. 28 depicts the post dilate to fracture for the four scaffold designs. The post dilate to fracture is the diameter immediately prior to fracture (mm) when the crimped scaffold or scaffold segment is expanded by the balloon.

Figure 29:
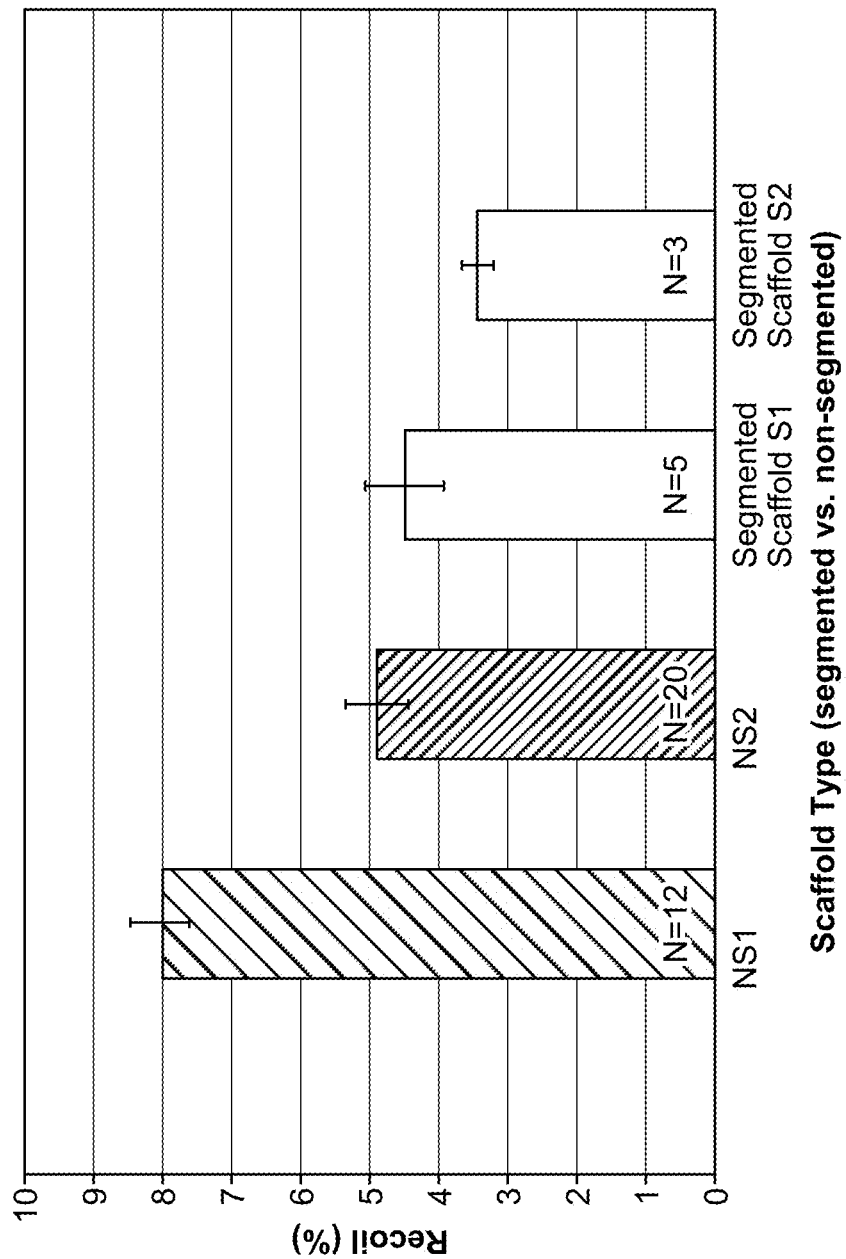
FIG. 29 depicts the scaffold diameter acute recoil after deployment for segmented and non-segmented scaffold designs.

FIG. 29 depicts the scaffold diameter recoil after deployment for the four scaffold designs. Each scaffold is dilated to 6 mm by the balloon. The balloon is deflated, removing the radial outward force on the scaffolds. The removal of the radial outward force results in recoil inward of the scaffolds. The S1 and S2 designs have larger radii in the corners which is believed to reduce the amount of plastic deformation and cracks. It is believed that the closed diamond pattern of S1 and S2 tends to hold its shape better than an open zig-zag pattern.

Figure 30:
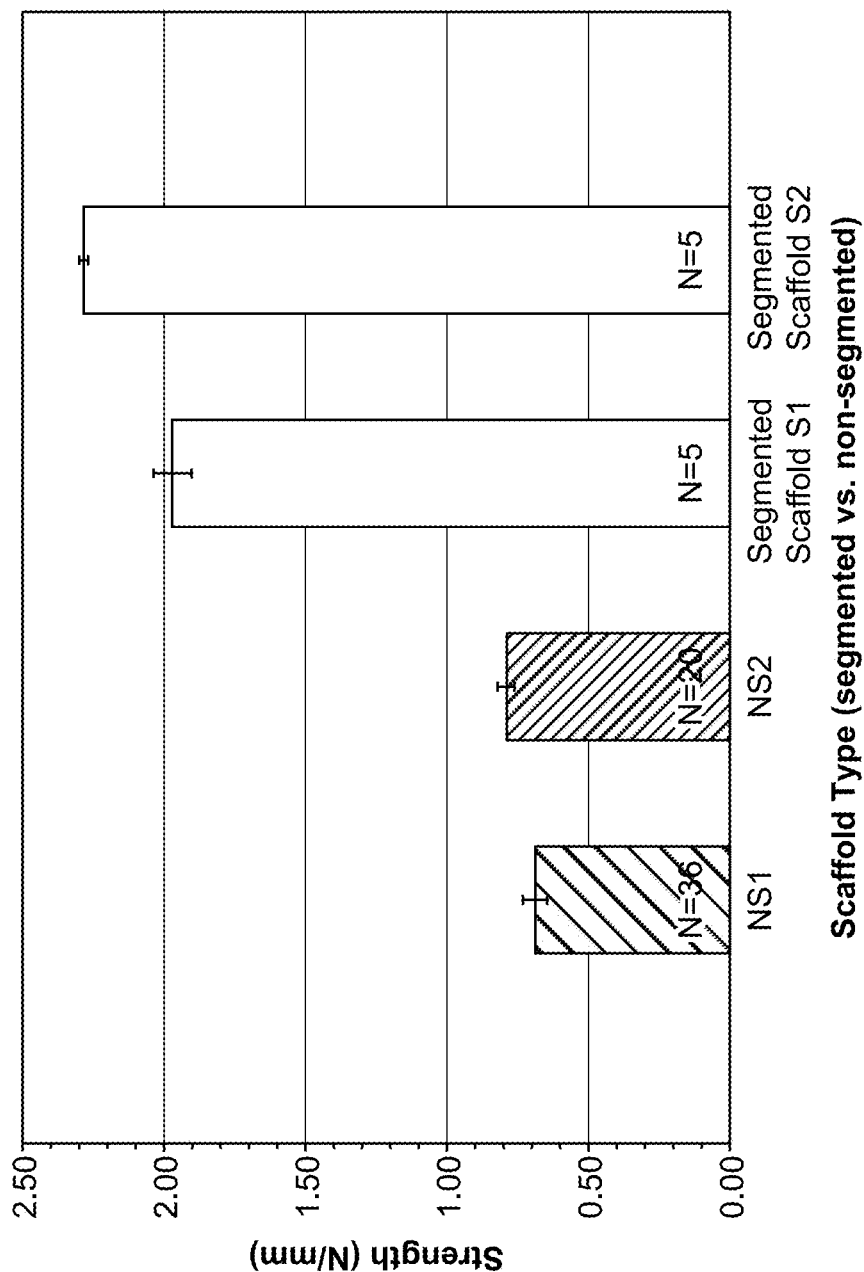
FIG. 30 depicts radial strength in Newton/mm of segmented and non-segmented scaffold designs.

FIG. 30 depicts the radial strength of the scaffold designs. The S2 design is stronger in the radial direction. In general, the tightly packed diamond shape is more than double the wider ring spaced zig-zag patterns.

Figure 31:
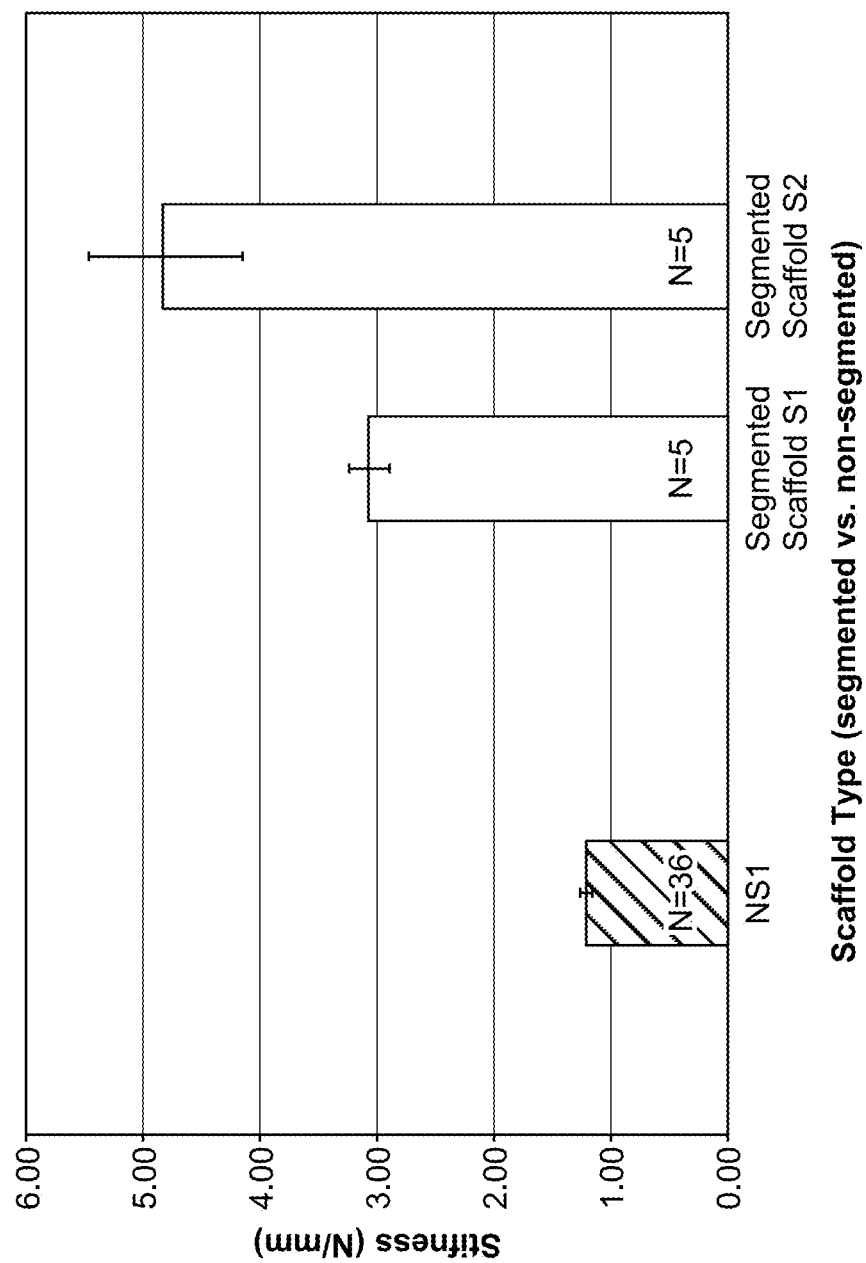
FIG. 31 depicts the radial stiffness in Newton/mm of segmented and non-segmented scaffold designs.

FIG. 31 depicts the radial stiffness of the scaffold designs.

Figure 32:
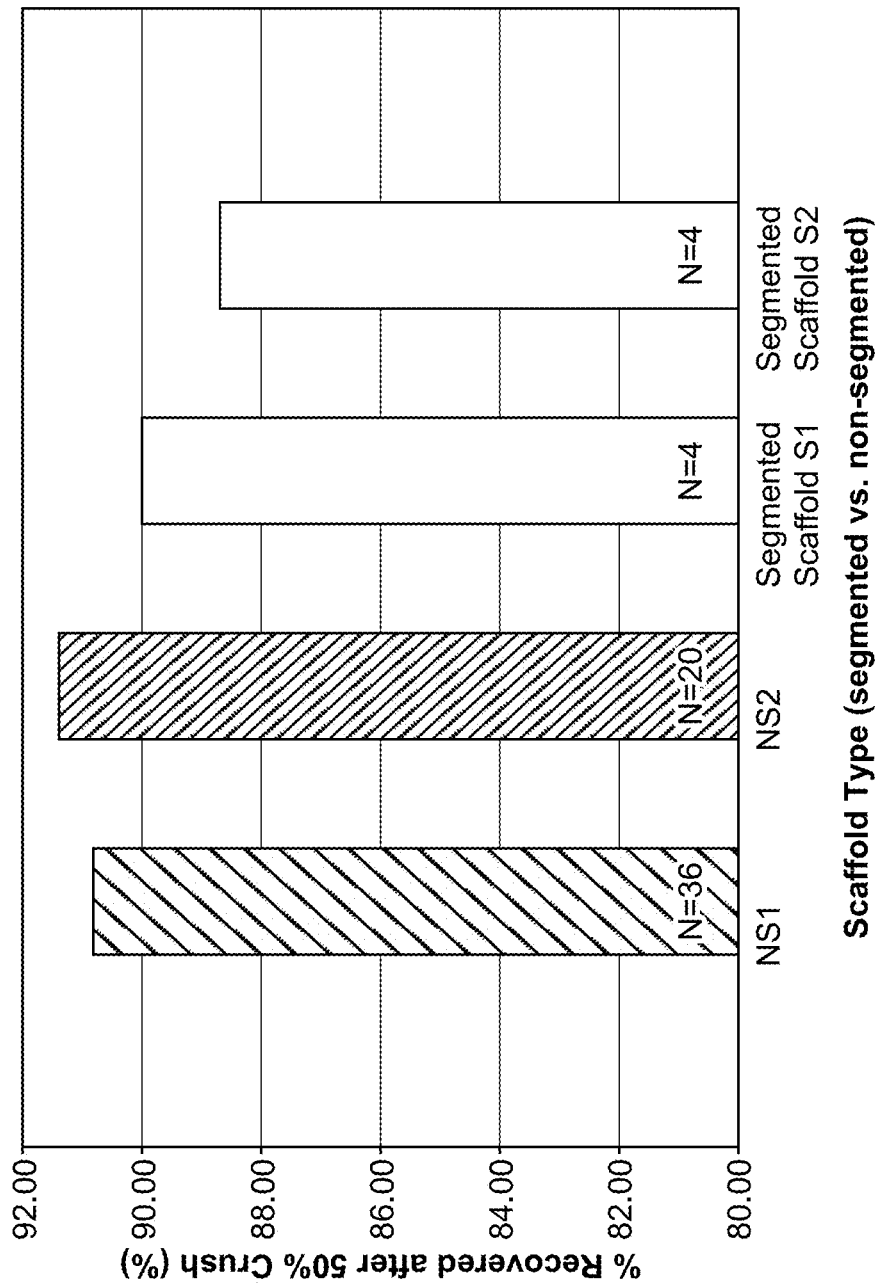
FIG. 32 depicts the crush recovery of segmented and non-segmented scaffold designs.

FIG. 32 depicts the crush recovery of the scaffold designs. The scaffolds were subjected to a pinching force which compresses the scaffolds to 50% of original diameter followed by release of the force. The crush recovery is the degree to which the scaffold recovered its original diameter.

Example 5: Animal Study Results for Implanted Segmented Scaffold Designs

Table 5 provides mean fracture counts for implanted segmented scaffolds for the S1 and S2 designs. The fracture counts were obtained from explanted scaffolds from a porcine model. The specimens were explanted 28 days after implantation. The S1 and S2 designs are compared with two non-segmented scaffold designs, NS1 and NS2. The S1 and S2 designs exhibited no strut discontinuities at 28 days post implant. The NS1 and NS2 designs had between 40 and 43 strut discontinuities in the same time period.

TABLE 5

Mean fracture counts of scaffolds explanted from porcine model after 28 days.

| Design | Mean Strut Fracture Count | | |
|---|---|---|---|
| | Ring | Link | Total |
| S1 | 0.7 | 0 | 0.7 |
| S2 | 0 | 0 | 0 |
| NS1 | 38 | 5 | 43 |
| NS2 | 36 | 4 | 40 |

Table 6 shows the late lumen loss of the S1 and S2 designs explanted from porcine model after 28 days along with results for the non-segmented designs.

TABLE 6

Late lumen loss of scaffolds explanted from porcine model after 28 days.

| Design | Late Lumen Loss (mm) |
|---|---|
| S1 | 1.02 |
| S2 | 1.18 |
| NS1 | 1.71 |
| NS2 | 1.42 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method, comprising:
    crimping a plurality of scaffold segments to a balloon, wherein the crimped segments are disconnected from each other and arranged end to end over the balloon;
    wherein ends of adjacent segments are separated by a gap having a gap size, the balloon has an outer surface comprising a gap region located at the gap and the gap region has a width no greater than the gap size; and
    disposing a coating comprising an antiproliferative drug only at the gap region.

2. The method of claim 1, wherein when the segments are crimped to the balloon the gaps have a first size, when the segments are radially expanded by the balloon the gaps have a second size, and wherein the first size is equal to the second size.

3. The method of claim 1, wherein the gap region comprises bands of raised balloon material.

4. The method of claim 1, wherein the plurality of scaffolds are formed from a tube or sheet of polymer material; and
    a segment of the segments comprises a first ring and a second ring adjoined to the first ring, and a link connects a crest of the first ring to a trough of the second ring, and wherein the plurality of rings are arranged to form diamond-shaped elements.

5. The method of claim 1, wherein a segment of the segments comprises a plurality of diamond-shaped elements.

6. The method of claim 1, wherein the antiproliferative drug includes paclitaxel, protaxel, taxotere, docetaxel, ortataxel, everolimus, sirolimus, myolimus, novolimus, temsirolimus, merilimus, deforolimus, or zotarolimus.

7. The method of claim 1, further including forming pillowed balloon portions at the gap regions.

8. The method of claim 7, wherein the drug is disposed after forming the pillowed portions.

9. The method of claim 1, wherein the drug is disposed at the gap regions after crimping the segments to the balloon.

10. The method of claim 9, wherein the segments are shielded when the drug is disposed at the gap regions.

11. The method of claim 1, wherein the drug is selectively applied only at the gap regions.

12. The method of claim 1, wherein the antiproliferative drug is disposed only at the gap region before or after the segments are crimped to the balloon.

13. The method of claim 1, wherein the balloon's gap region comprises a pre-pillowed portion of the balloon.

* * * * *